(12) United States Patent
Mirtsching et al.

(10) Patent No.: US 8,050,462 B2
(45) Date of Patent: *Nov. 1, 2011

(54) METHODS AND SYSTEMS FOR ADMINISTERING A DRUG PROGRAM

(75) Inventors: Warren Mirtsching, Fort Collins, CO (US); John Felix, Berthoud, CO (US); Mark A. Gustafson, Windsor, CO (US)

(73) Assignee: JBS USA, LLC, Greeley, CO (US)

( * ) Notice: Subject to any disclaimer, the term of this patent is extended or adjusted under 35 U.S.C. 154(b) by 205 days.

This patent is subject to a terminal disclaimer.

(21) Appl. No.: 12/575,964

(22) Filed: Oct. 8, 2009

(65) Prior Publication Data

US 2010/0027849 A1    Feb. 4, 2010

Related U.S. Application Data

(63) Continuation of application No. 11/695,712, filed on Apr. 3, 2007, now Pat. No. 7,613,330, and a continuation of application No. 11/695,568, filed on Apr. 2, 2007, now Pat. No. 7,606,394.

(60) Provisional application No. 60/789,013, filed on Apr. 3, 2006, provisional application No. 60/868,641, filed on Dec. 5, 2006.

(51) Int. Cl.
*G06K 9/00* (2006.01)
*G08B 21/00* (2006.01)
*G08B 23/00* (2006.01)

(52) U.S. Cl. ............... 382/110; 340/540; 340/573.1; 345/628

(58) Field of Classification Search ............ 382/110; 340/540, 573.1
See application file for complete search history.

(56) References Cited

U.S. PATENT DOCUMENTS

| | | | |
|---|---|---|---|
| 1,337,334 | A | 3/1886 | Jones et al. |
| 1,485,755 | A | 3/1924 | Alcock |
| 1,900,573 | A | 3/1933 | McArthur |
| 2,544,681 | A | 3/1951 | Harsham et al. |
| 2,544,724 | A | 3/1951 | Rentschler |
| 2,621,362 | A | 12/1952 | Cosden |
| 2,870,018 | A | 1/1959 | Williams |
| 2,879,539 | A | 3/1959 | Cervin |
| 2,979,411 | A | 4/1961 | Pircon |
| 3,314,103 | A | 4/1967 | Rains |
| 3,537,130 | A | 11/1970 | McDonnell |
| 3,626,550 | A | 12/1971 | Troy |

(Continued)

FOREIGN PATENT DOCUMENTS

AU    760810    5/2003

(Continued)

OTHER PUBLICATIONS

Boleman, National Beef Quality Audit—1995: Survey of Producer-Related Defects and Carcass Quality and Quantity Attributes, J. Anim. Sci. 76:96-103 (1998).

(Continued)

*Primary Examiner* — John Strege
(74) *Attorney, Agent, or Firm* — Sheridan Ross P.C.

(57) ABSTRACT

Systems and methods are described that provide a fast and simple way of administering a drug program related to an animal. Specifically, systems are provided that can receive, compile and analyze information regarding the condition of an organ in a form that is readily readable, transferable to others, and associated with, or linked to, other information such as the presence or absence of an administered drug, combination of drugs, or drug program.

23 Claims, 14 Drawing Sheets

U.S. PATENT DOCUMENTS

| | | |
|---|---|---|
| 3,657,770 A | 4/1972 | Wallace |
| 3,736,622 A | 6/1973 | Wallace |
| 3,863,294 A | 2/1975 | Barbee |
| 4,023,574 A | 5/1977 | Nemec |
| 4,221,021 A | 9/1980 | Swilley |
| 4,307,490 A | 12/1981 | Watkins et al. |
| 4,340,993 A | 7/1982 | Cook |
| 4,358,872 A | 11/1982 | VanZandt |
| 4,495,676 A | 1/1985 | Hartmetz, II |
| 4,561,149 A | 12/1985 | Nijhuis |
| 4,675,947 A | 6/1987 | Clatfelter et al. |
| 4,733,971 A | 3/1988 | Pratt |
| 4,774,741 A | 10/1988 | Bernharadt et al. |
| 4,815,042 A | 3/1989 | Pratt |
| 4,827,727 A | 5/1989 | Caracciolo |
| 4,860,403 A | 8/1989 | Webb et al. |
| 4,889,433 A | 12/1989 | Pratt |
| 4,910,024 A | 3/1990 | Pratt |
| 4,931,933 A | 6/1990 | Chen et al. |
| 5,007,336 A | 4/1991 | Bernhardt et al. |
| 5,008,821 A | 4/1991 | Pratt et al. |
| 5,167,569 A | 12/1992 | Davis |
| 5,219,244 A | 6/1993 | Skeels |
| 5,282,940 A | 2/1994 | Griffis et al. |
| 5,315,505 A | 5/1994 | Pratt et al. |
| 5,340,211 A | 8/1994 | Pratt |
| RE34,776 E | 11/1994 | Pratt |
| 5,369,032 A | 11/1994 | Pratt |
| 5,401,501 A | 3/1995 | Pratt |
| 5,478,990 A | 12/1995 | Montanari et al. |
| 5,486,145 A | 1/1996 | Te Dorsthorst et al. |
| 5,512,014 A | 4/1996 | Burnett |
| 5,529,793 A | 6/1996 | Garner et al. |
| 5,534,271 A | 7/1996 | Ware et al. |
| 5,573,002 A | 11/1996 | Pratt |
| 5,595,066 A | 1/1997 | Zwanikken et al. |
| 5,668,634 A | 9/1997 | Newman |
| 5,673,647 A | 10/1997 | Pratt |
| 5,704,830 A | 1/1998 | Van Ochten |
| 5,803,906 A | 9/1998 | Pratt et al. |
| 5,836,880 A | 11/1998 | Pratt |
| 5,855,507 A | 1/1999 | Fisher et al. |
| 5,879,732 A | 3/1999 | Caracciolo, Jr. et al. |
| 5,888,132 A | 3/1999 | Burnett |
| 5,899,802 A | 5/1999 | Burnett |
| 5,958,714 A | 9/1999 | Gordon et al. |
| 6,000,361 A | 12/1999 | Pratt |
| 6,001,655 A | 12/1999 | Spadaro et al. |
| 6,019,674 A | 2/2000 | Austin |
| 6,084,407 A | 7/2000 | Ellis |
| 6,104,966 A | 8/2000 | Haagensen |
| 6,120,367 A | 9/2000 | Scott et al. |
| 6,131,744 A | 10/2000 | Pratt |
| 6,135,055 A | 10/2000 | Pratt |
| 6,159,090 A | 12/2000 | Thompson |
| 6,190,250 B1 | 2/2001 | Volk et al. |
| 6,198,834 B1 | 3/2001 | Belk et al. |
| 6,200,210 B1 | 3/2001 | Pratt |
| 6,231,435 B1 | 5/2001 | Pilger |
| RE37,266 E | 7/2001 | Te Dorsthorst et al. |
| 6,290,592 B1 | 9/2001 | Allen et al. |
| 6,318,289 B1 | 11/2001 | Pratt |
| 6,322,436 B2 | 11/2001 | Potter et al. |
| 6,342,839 B1 | 1/2002 | Curkendall |
| 6,364,759 B2 | 4/2002 | Allen et al. |
| 6,458,024 B1 | 10/2002 | Potter et al. |
| 6,478,667 B2 | 11/2002 | Bell et al. |
| 6,516,746 B2 | 2/2003 | Pratt |
| 6,519,954 B1 | 2/2003 | Prien et al. |
| 6,546,304 B2 | 4/2003 | Thorvaldsson et al. |
| 6,547,726 B2 | 4/2003 | Pratt et al. |
| 6,579,236 B2 | 6/2003 | Pratt |
| 6,592,517 B2 | 7/2003 | Pratt et al. |
| 6,648,744 B2 | 11/2003 | Bell et al. |
| 6,712,685 B2 | 3/2004 | Potter et al. |
| 6,724,309 B2 | 4/2004 | Grose et al. |
| 6,736,272 B2 | 5/2004 | Pratt |
| 6,796,892 B2 | 9/2004 | Allen et al. |
| 6,859,672 B2 | 2/2005 | Roberts et al. |
| 6,891,961 B2 | 5/2005 | Eger et al. |
| 6,896,607 B2 | 5/2005 | Potter et al. |
| 6,912,434 B2 | 6/2005 | van den Nieuwelaar et al. |
| 6,975,223 B1 | 12/2005 | Mladen et al. |
| 6,975,233 B2 | 12/2005 | Grose et al. |
| 7,022,005 B2 | 4/2006 | Potter et al. |
| 7,025,669 B2 | 4/2006 | Richards |
| 7,063,836 B2 | 6/2006 | Garner et al. |
| 7,107,936 B2 | 9/2006 | Fantin et al. |
| 7,108,882 B2 | 9/2006 | Schaefer et al. |
| 7,207,289 B2 | 4/2007 | Montgomery |
| 7,338,356 B2 | 3/2008 | Bell et al. |
| 7,364,503 B2 | 4/2008 | Bell et al. |
| 7,400,256 B2 | 7/2008 | Knopik et al. |
| 7,440,901 B1 | 10/2008 | Dlott et al. |
| 7,606,394 B2 | 10/2009 | Mirtsching |
| 7,613,330 B2 | 11/2009 | Mirtsching et al. |
| 2003/0154729 A1 | 8/2003 | Prien et al. |
| 2004/0026920 A1 | 2/2004 | Meischen |
| 2004/0115322 A1 | 6/2004 | Osborn |
| 2005/0042980 A1 | 2/2005 | Allen et al. |
| 2005/0049518 A1 | 3/2005 | Nel |
| 2005/0181720 A1 | 8/2005 | Osborn et al. |
| 2005/0186896 A1 | 8/2005 | Nielsen |
| 2005/0272057 A1 | 12/2005 | Abrahamsen et al. |
| 2006/0041408 A1 | 2/2006 | McGoogan et al. |
| 2006/0041412 A1 | 2/2006 | Engelke et al. |
| 2006/0041413 A1 | 2/2006 | Burghardi et al. |
| 2006/0041419 A1 | 2/2006 | Newcomb et al. |

FOREIGN PATENT DOCUMENTS

| | | |
|---|---|---|
| AU | 2003272338 | 3/2004 |
| CA | 2372042 | 11/2000 |
| CA | 2497726 | 3/2004 |
| EP | 0090478 | 10/1983 |
| EP | 0353199 | 1/1990 |
| EP | 1175151 | 1/2002 |
| FR | 2495438 | 6/1982 |
| FR | 2519846 | 7/1983 |
| GB | 1478258 | 6/1977 |
| GB | 2147791 | 5/1985 |
| JP | 8009876 | 1/1996 |
| JP | 8023869 | 1/1996 |
| SU | 0833182 | 5/1981 |
| SU | 1009382 | 4/1983 |
| SU | 1391566 | 4/1988 |
| WO | WO 81/01641 | 6/1981 |
| WO | WO 98/19550 | 5/1998 |
| WO | WO 01/54509 | 8/2001 |
| WO | WO 01/95716 | 12/2001 |
| WO | WO 02/47485 | 6/2002 |
| WO | WO 02/058474 | 8/2002 |
| WO | WO 2004/021782 | 3/2004 |
| WO | WO 2004/085997 | 10/2004 |
| WO | WO 2005/099466 | 10/2005 |

OTHER PUBLICATIONS

Bosilevac, Development and Evaluation of an On-Line Hide Decontamination Procedure for Use in a Commercial Beef Processing Plant, Journal of Food Protection, vol. 68, No. 2, 2005, pp. 265-272.

Clare, Improving Tenderness of Normal and Callipyge Lambs with Calcium Chloride, J. Anim. Sci. 75:377-385 (1997).

Cross, Influence of Breed, Sex, Age and Electrical Stimulation on Carcass and Palatability Traits of Three Bovine Muscles, Journal of Animal Science, vol. 58, No. 6, 1984, pp. 1358-1365.

Crouse, The Effect of Carcass Electrical Stimulation on Meat Obtained From Bos Indicus and Bos Taurus Cattle, Journal of Food Quality, 10, 1987, pp. 407-416.

Davey, Carcass Electrical Stimulation to Prevent Cold Shortening Toughness In Beef, Refrigeration Science and Technology, 1977, pp. 293-298.

Ducastaing, Effects of Electrical Stimulation on Post-mortem Changes in the Activities of Two Ca Dependent Neutral Proteinases and their Inhibitor in Beef Muscle, Meat Science 15, 1985, pp. 193-202.

Eikelenboom, The Effect of High and Low Voltage Electrical Stimulation on Beef Quality, Meat Science 15, 1985, pp. 247-254.

Eilers, Modification of Early-Postmortem Muscle pH and Use of Postmortem Aging to Improve Beef Tenderness, J. Anim. Sci., 74:790-798 (1996).

Epley, Meat Tenderness, retrieved from website http://www.extension.umn.edu/distribution/nutrition/DJ0856 on Apr. 4, 2006, 8 pages.

Fabiansson, The Influence of Low Voltage Electrical Stimulation on Some Physical and Sensoric Properties of Beef, Acta Agric Scand, 34:368-376 (1984).

Federal Register, Cooling and Chilling Requirements for Raw Meat and Poultry, vol. 61, No. 144, p. 38856 (Jul. 25, 1996).

Ferguson, Meat Standards Australia, A 'PACCP' Based Beef Grading Scheme for Consumers, 3) PACCP Requirements that Apply to Carcass Processing, 45th International Congress of Meat Science and Technology, Yokohama, Japan, 45:18-19 (1999).

Hildrum, Combined Effects of Chilling Rate, Low Voltage Electrical Stimulation and Freezing on Sensory Properties of Bovine M. Longissimus Dorsi, Meat Science 52, 1999, pp. 1-7.

Kerth, Electrical Stimulation Effects on Tenderness of Five Muscles from Hampshire x Rambouillet Crossbred Lambs with the Callipyge Phenotype, J. Anim. Sci., 77:2951-2955 (1999).

McKeith, Tenderness Improvement of the Major Muscles of the Beef Carcass by Electric Stimulation, Journal of Food Science, vol. 46, 1981, pp. 1774-1776.

McNeal, Effects of Stunning and Decapitation on Broiler Activity During Bleeding, Blood Loss, Carcass, and Breast Meat Quality, Poultry Science 82:163-168 (2003).

Miller, Bovine Longissimus dorsi Muscle Glycogen and Color Response as Affected by Dietary Regimen and Post-Mortem Electrical Stimulation in Young Bulls, Meat Science 19, 1987, pp. 253-263.

Morgan, National Beef Tenderness Survey, J. Anim. Sci. 69:3274-3283 (1991).

Northcutt, Reference Guide for Solving Poultry Processing Problems, Bulletin 1156, May 1997, The University of Georgia College of Agricultural and Environmental Sciences, 6 pages.

Purchas, Effects of Growth Potential and Growth Path on Tenderness of Beef Longissimus Muscle From Bulls and Steers, J. Anim. Sci. 80:3211-3221 (2002).

Roeber, Effects of a Unique Application of Electrical Stimulation on Tenderness, Color, and Quality Attributes of the Beef Longissimus Muscle, J. Anim. Sci., 78:1504-1509 (2000).

Savell, Effect of Electrical Stimulation on Palatability of Beef, Lamb and Goat Meat, Journal of Food Science, vol. 42, No. 3, 1977, pp. 702-706.

Stiffler, Electrical Stimulation Purpose, Application, and Results, Bulletin, Texas Agricultural Extension Service, 1982, pp. 1-8.

Takahashi, Effects of Low-Frequency Electrical Stimulation on Beef Tenderness, Meat Science 11, 1984, pp. 207-225.

Tatum, New Approaches for Improving Tenderness, Quality, and Consistency of Beef, Proceedings of the American Society of Animal Science, 1999, 10 pages.

Westervelt, Relationship Among Spinal Cord Severing, Electrical Stimulation and Postmortem Quality Characteristics of the Porcine Carcass, Journal of Animal Science, vol. 46, No. 5, 1978, pp. 1206-1211.

"US traceback system debate", available at http://www.ellinghuysen.com/news/articles/26845.shtml, printed Jan. 6, 2006, pp. 1-2.

"Beef Traceability Case Study", GS1 Ireland, Feb. 2005, 24 pages.

MICOTIL 300—Section 1—Chemical Product and Company, Elanco, effective date Feb. 8, 2006, pp. 1-9.

Pulmotil Medicated Premix—Section 1—Chemical Product and Company, Elanco, effective date Nov. 18, 2003, pp. 1-9.

"Environmental Assessment—INAD 9087—Zilpaterol Hydrochloride Type A Medicated Article (Premix) in Confinement Cattle", Sponsor Intervet Inc., Nov. 2001, pp. 1-14.

Optaflexx 45—Ractopamine Hydrochloride, Elanco, Apr. 11, 2004, pp. 1-2.

"What is Bovamine?", Nutrition Physiology Corporation, available at http://www.bovamine.com/products.html, printed Feb. 7, 2007, 2 pages.

Wines "Pig Organs Tainted With a Banned Steroid Sicken 70 in China", MY Times, Feb. 24, 2009, 2 pages.

International Search Report for International (PCT) Patent Application No. PCT/US07/08472, mailed Sep. 30, 2008.

Written Opinion for International (PCT) Patent Application No. PCT/US07/08472, mailed Sep. 30, 2008.

International Preliminary Report on Patentability for International (PCT) Patent Application No. PCT/US07/08472, mailed Dec. 11, 2008.

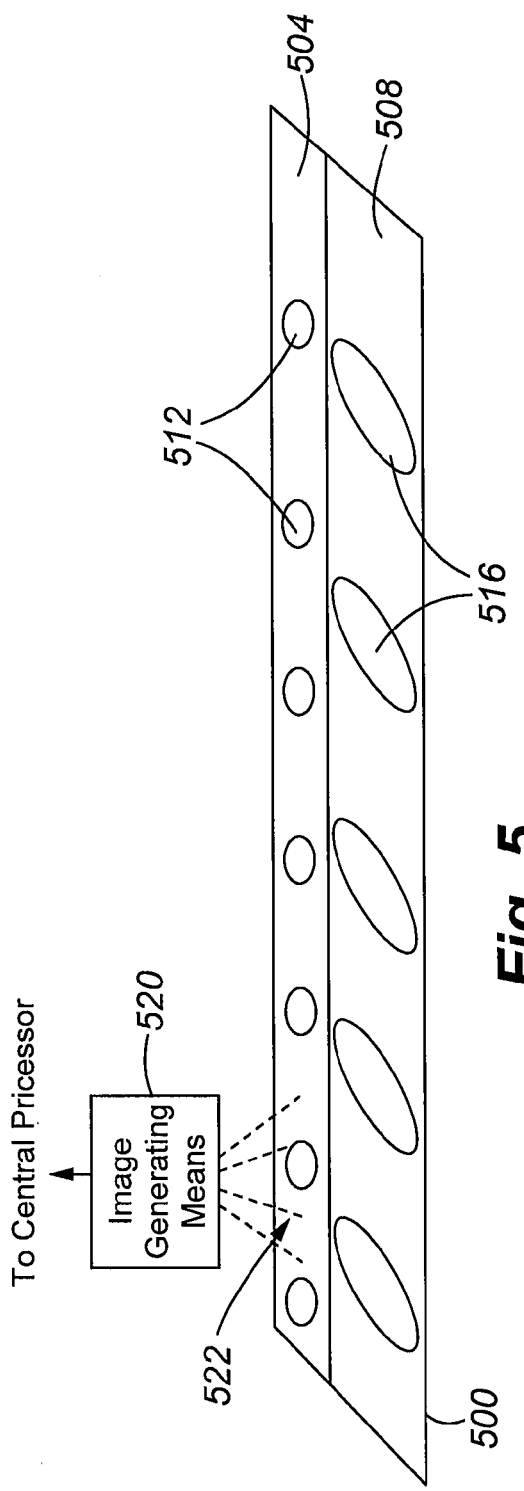
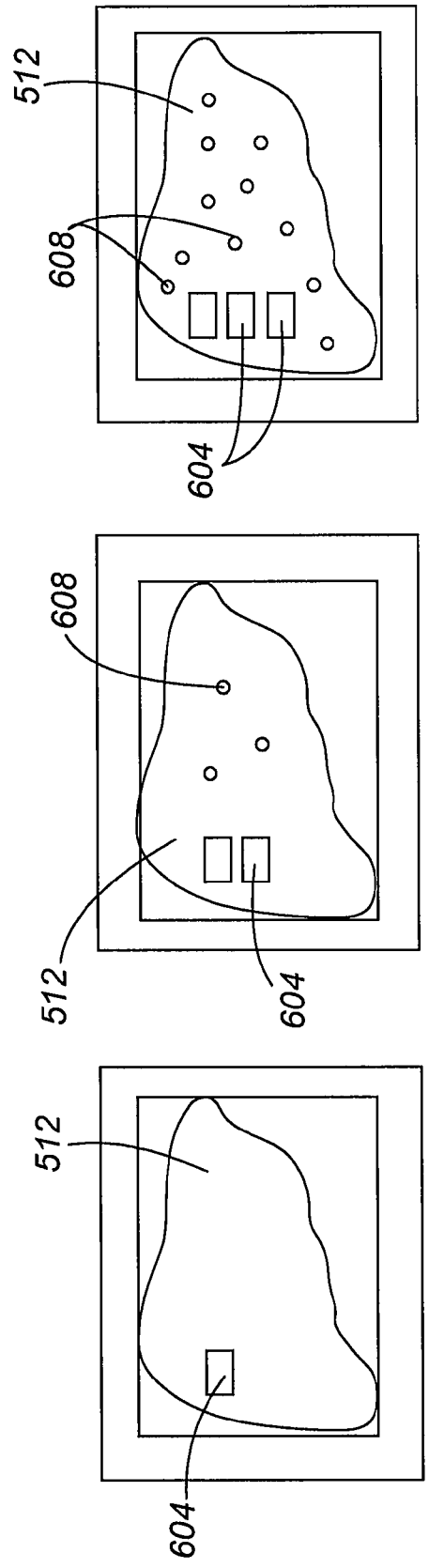
Fig. 5
Fig. 6A
Fig. 6B
Fig. 6C

METHODS AND SYSTEMS FOR ADMINISTERING A DRUG PROGRAM

CROSS REFERENCE TO RELATED APPLICATIONS

The present application is a continuation application of U.S. patent application Ser. No. 11/695,712, filed on Apr. 3, 2007, and claims the benefit of U.S. patent application Ser. No. 11/695,568, filed Apr. 2, 2007. The present application also claims the benefits of U.S. Provisional Application Ser. No. 60/789,013 filed on Apr. 3, 2006, entitled "Method and System for Tracking and Managing Livestock Through the Production Process" and U.S. Provisional Application Ser. No. 60/868,641 filed on Dec. 5, 2006, entitled "Method and System for Administering a Drug Program Related to Livestock," all of such references are incorporated herein in their entirety by this reference.

FIELD OF THE INVENTION

The present invention generally relates to methods and systems for administering a drug program, including those directed to livestock.

BACKGROUND OF THE INVENTION

During commercial meat production, livestock carcasses are subjected to a number of slaughtering procedures that result in the dissection of an intact animal into a plurality of carcasses and meat products. In order to facilitate production, the carcasses may be attached to a trolley or shackle at different points along the meat processing line so that they may move quickly along the production line in a controlled manner. As they move through production, the carcasses are commonly tracked, identified and inspected at a number of locations, where certain information concerning the health or quality of the carcasses, and of the animals they are derived from, may be ascertained and recorded.

Livestock carcasses and meat products are tracked for a variety of reasons, including monitoring the efficiency of a meat production facility and the safe handling and processing of the carcasses and meat products. Meat producers have therefore instituted tracking systems in meat processing plants which utilize a unique identifier for each carcass that enters the meat processing line so that the carcass, and the meat products derived from it, may be tracked as they move along the processing line. The information collected may be used for a variety of purposes, including sorting carcasses before they are broken down into meat products for packaging and tracking carcass information back to the producer of the animal. The collection of information is not limited to the processing plant, but may also be ascertained at numerous-locations within a feedlot, farm or ranch. In many instances, this information is collected and analyzed by hand, at a considerable cost to the collecting party, and the information is difficult to obtain in a consistent manner over time, as personnel changes, inconsistencies in training, and individual variations in the collection and presentation of information make consistent collection difficult.

By way of example, beef livers that are isolated as a meat product from carcasses are typically individually hand inspected by representatives of the United States Department of Agriculture along the meat processing line. During this inspection, the inspector is present in the processing plant so that each liver can be visually inspected and given a quality grade, which inspection may include observing a liver as it passes by and/or picking up a liver in order to view one or more sides. The inspector places one or more stamps on the liver, indicating the grade given, such as sufficient for human consumption (one stamp) or sufficient for animal consumption (two stamps), both of which are profitable grades as the liver may be processed and delivered for sale to consumers. The inspector may also grade a liver as inedible or condemned (three stamps), which represents a complete financial loss as all of these livers must be destroyed. A liver may be graded as inedible or condemned for a variety of reasons, including, without limitation, the presence of abscesses resulting from a fast conversion to a high protein diet in advance of slaughter. While all condemned livers result in a financial loss, this type of condemned liver is of particular concern as they represent the vast majority of condemned livers, yet their condition is preventable in live animals prior to slaughter, via the use of commercially available drugs. If this type of liver is treated prior to slaughter, it may then represent a profit as it is more likely to be graded in such a way as to allow sale to consumers, rather than graded as condemned. There are several commercially available drugs that may be used to treat and prevent the presence of abscesses in beef livers that result from a fast conversion to a high protein diet in advance of slaughter, such as the antibiotic macrolide tylosin, among others.

SUMMARY OF THE INVENTION

Methods and systems for administering a drug program are provided. Although well suited for use in the production of bovine meat products, and particularly organs, advantages offered by the present invention may be realized in processes related to animals other than just livestock, where the compilation, analysis and transmission of information relating to particular organs is desired.

As used herein, "animals" refers to all animals, including but not limited to the many forms of commercially useful livestock. An "animal" refers to a single intact animal and, as such, may be a live animal, though that is not required. A "carcass" is a part or portion of an animal. An "organ" is an internal organ derived from an animal, including, but not limited to, brain, liver, tongue, pancreas gland, thymus gland, stomach, feet, kidney, lungs, heart, small intestine, testicles, or placenta. Although the systems and methods of the present invention have been found particularly applicable to livers and lungs, the systems and methods can be employed to collect, compile and analyze data from all organs and it is to be expressly understood that other organs, such as those listed above, can be used with the present invention. The terms "drug" and "combination of drugs" are used herein in their broadest sense and include, without limitation, any biological or chemical substance, synthetic or non-synthetic, that is isolated, purified and/or synthesized and subsequently administered to, and/or taken by, an organism for non-dietary needs in order to produce some effect(s) or to alter some bodily function(s) such as relieving symptoms, curing diseases, eliciting preventative effects, or any other purpose. A "drug program" includes the giving or administration of drugs to animals, the giving or administering of a combination of drugs to animals, the giving or administering of a single drug or a combination of drugs to a single animal or a combination of animals, any combination of the foregoing, and/or the timing of such giving or administration. "Linking" and/or "linked" includes the standard means of computer-assisted storage, analysis, compilation and display of data or information in a database or similar storage/archiving facility, whereby one or more data points is tagged or identified with an electronic signature or data pointer so that it is readily readable by a computer and such that it can be readily associated or joined with other data points, whether such other data points are in the same database or a different one. The electronic signatures or data pointers may be used to quickly pull specific data points from large pools of information, associate it with other data points that may be similarly pulled from large data pools, and then analyze and/or compile a plurality of specific data points into a readable format that is readily transmissible via standard electronic means.

Moreover, many companies focus on supplying dietary drugs, combinations of drugs and the like. These companies usually claim that their product will help the animals be healthier. These types of companies may also be interested in receiving feedback related to various portions of the animals. For example, a company that supplies drugs or combinations of drugs aimed at reducing the number of organ abnormalities may be interested in knowing how many organ abnormalities were present in animals that were treated with their product and how many organ abnormalities were present in others who did not receive their product. Many of these companies pay individuals non-trivial amounts of money to gather this sort of information. Using at least some embodiments of the present invention, a drug company can purchase information relating to certain portions of an animal that was treated with their drugs or combinations of drugs. This information can be, for example, gathered automatically and/or continuously and thus can be provided back to the supplier much more quickly and in more volume than could be realized in the past.

Yet another aspect of the present invention is to provide a system that is compliant with government regulations and can be easily updated and expanded to be in compliance with new government regulations. For example, as new laws are passed that potentially restrict meat production processes, it is important for meat producers to know that they can change as the rules change without requiring too many costs. Embodiments of the present invention provide for a relatively easily scalable and upgradeable system.

An additional aspect of the present invention is directed to presenting information regarding the condition of an organ in a form that is readily readable, transferable to others, and associated with, or linked to, other information. This may involve one or many steps, depending upon the manner in which the desired information is recorded. For example, the collected information may be entered into a computer or a server where it may be electronically manipulated, stored or disseminated with, or without, the linked information.

It is therefore an object of the present invention to provide accurate, identification systems that can receive, compile and analyze information about the health and quality of animals, and which can transmit that compiled and analyzed data to a database for storage and/or archiving. Such systems will have the benefit of collecting and presenting information in a consistent and cost effective manner, making it superior to the collection and presentation of the same information by hand or by other methods presently in existence.

Drug companies will also benefit from such systems and from such methods as they will be able to purchase and/or acquire reports that allow them to quickly and easily determine whether certain drugs, combinations of drugs, and/or drug programs: have been administered to one or more animals and/or actually serve to increase the health of animals. Statistical information that can be compiled and reported using certain embodiments of the present invention will thus serve to either reinforce the efficacy of certain drugs or combinations of drugs, or will allow the drug company to assess whether certain, less efficacious drugs or combinations of drugs need further research and development, or whether such drugs or combinations of drugs should be removed from the marketplace entirely. As with meat producers, drug companies will be able to utilize certain embodiments of the present invention to collect and analyze data points concerning each of the above-referenced categories, as well as many others, and will be able to quickly and easily compile and analyze these data points to generate reports, or acquire generated reports concerning the same. Similarly, comparison reports can be generated that are derived from animals that have received certain drugs, combinations of drugs, and/or drug programs with those that received drugs, combination of drugs, and/or drug programs produced by competitors. The present invention will also allow drug companies to determine whether certain drugs, combinations of drugs, and/or drug programs provide the desired results, whether a drug, combination of drugs, and/or drug program can be applied to a variety of species with positive results, and to test new drugs. By utilizing reports generated via the present invention, drug companies will be able to charge a price for a specific drug, combination of drugs, and/or drug program that is in accordance with its actual impact on animal health and will be able to market to those that are not utilizing their drugs.

In certain embodiments, the ability to provide visual evidence of results, such as an image of an organ containing abnormalities with identifying data, provides compelling and verifiable proof of how a drug, combination of drugs, and/or drug program (or the lack thereof) may have affected an animal. This knowledge will help ensure reasonable efforts to maximize the health.

Another object of the present invention is to provide systems that can electronically receive information regarding the origin and/or health of an animal, and preferably organs, from one or a plurality of locations, and then transmit that information electronically to a computer and/or server for analysis, compilation, transmission and/or storage. Such information may be useful to determine whether, or how, data identification of one abnormal organ may be used to track other organs from an individual animal.

Information regarding the origin and/or health of an animal may include, without limitation: the country, geographic region, state, county, city, or town of a single animal or a group of animals; results from a check-up and/or diagnosis of one or more animals; information concerning the use of a drug, combinations of drugs, or administration of a drug program; information concerning the general appearance of an animal or group of animals; the images of one or a plurality of animals; combinations of the same; and similar information. Information regarding the quality of preferably organs, may include, without limitation: one or a plurality of images of an organ; one or a plurality of similar images showing the presence of abscesses or similar medical maladies, if any: and similar information.

By way of example, an image of an organ, tagged with an electronic signature or data pointer and showing the absence of any abnormalities, may be readily linked to information of the time at which the image was generated, which may be further linked to information concerning the time at which that organ was dissected from a carcass.

In accordance with at least one embodiment of the present invention, a method for administering a drug program is provided. The method comprises the steps of: receiving information regarding the quality of an organ; receiving information regarding the origin of the organ; receiving information regarding the presence or absence of an administered drug in the animals located at the origin; linking such information together; and then, based on such linked information, determining whether the quality is due to, or has been influenced by, the presence or absence of an administered drug, combination of drugs, and/or drug program in the animals located at the origin.

In accordance with another embodiment of the present invention, the system comprises a facility comprising a database, a server, at least one means for generating an image, at least one external server, and at least one display apparatus. The database is used to store and/or archive a variety of information, including without limitation information concerning the health, quality, origin and/or the presence or absence of a drug in organs. The server may comprise one or more processors, memory, and is operable to determine the health, quality, origin and/or the presence or absence of a drug in an animal, or organ based on image information received from the image generation means, as well as the time and date such information was received. Additionally, the server is operable to receive, compile, analyze and/or link together information concerning the health, quality, origin and/or the presence or absence of a drug in the animals and/or organs from at least one the database, and is operable to transfer this information to at least one external server capable of receiving such information and to the database for storage and/or archiving. The means for generating images is/are operable to receive image information regarding organs and to transmit this information to the server, where it will be received, compiled, analyzed and transmitted to the database for storage and/or archiving and may also be transmitted to at least one external server capable of receiving the same.

These and other advantages will be apparent from the disclosure of the invention(s) contained herein. The above-described embodiments and configurations are neither complete nor exhaustive. As will be appreciated, other embodiments of the invention are possible using, alone or in combination, one or more of the features set forth above or described in detail below.

BRIEF DESCRIPTION OF THE DRAWINGS

FIG. 5 is a conveyor belt for transporting parts of an animal through the production process in accordance with at least some embodiments of the present invention;

FIG. 6A shows a high grade organ in accordance with at least some embodiments of the present invention;

FIG. 6B shows a medium grade organ in accordance with at least some embodiments of the present invention;

FIG. 6C shows a lower grade organ in accordance with at least some embodiments of the present invention;

DETAILED DESCRIPTION

Figure 1:
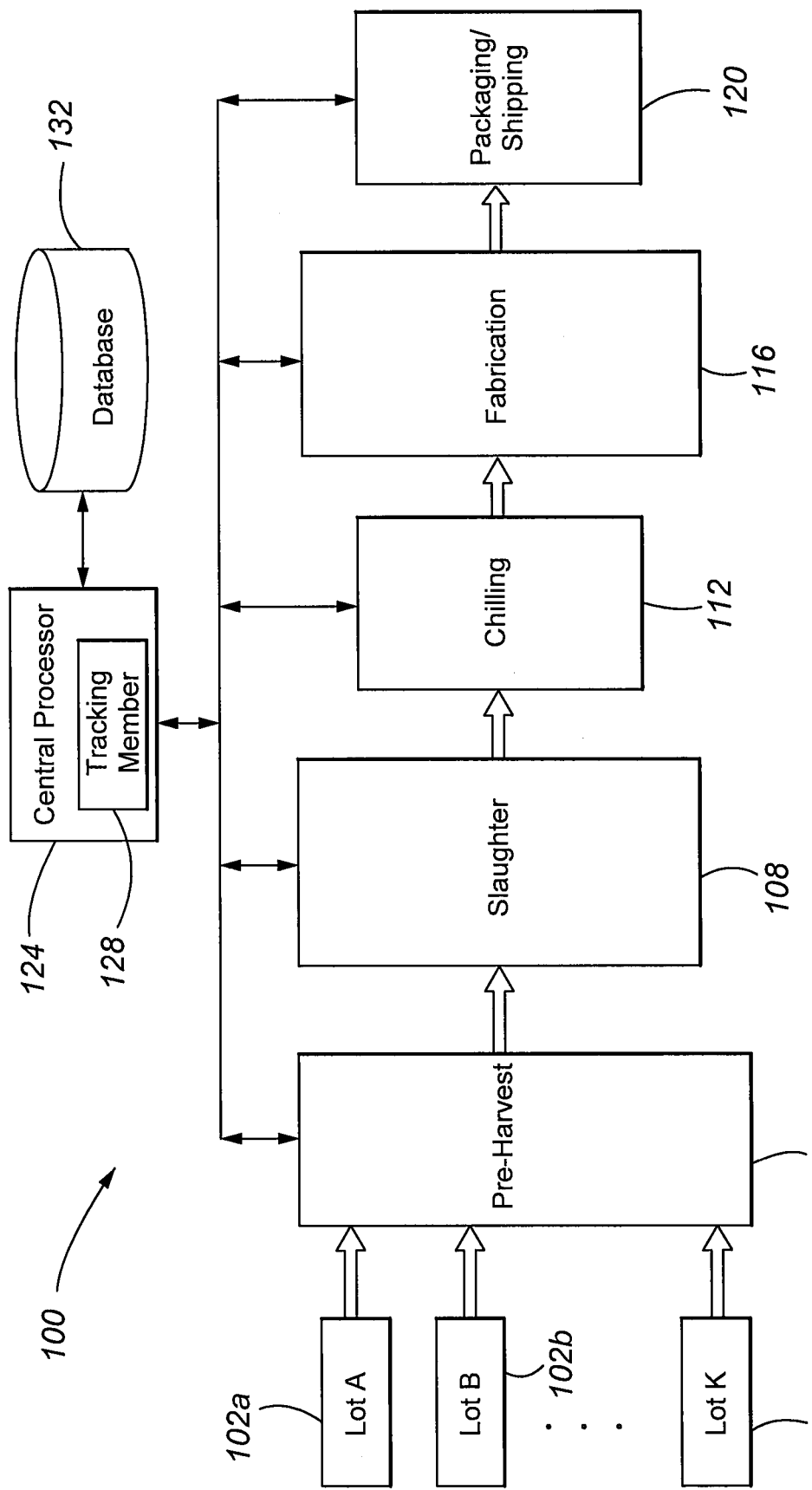
FIG. 1 is a block diagram of components of a meat production and tracking system in accordance with at least some embodiments of the present invention.

Referring initially to FIG. 1, a meat production and tracking system 100 will be described in accordance with embodiments of the present invention. The system 100, in the depicted embodiment, comprises a pre-harvest area 104, a slaughter area 108, a chilling area 112, a fabrication area 116, and a packaging/shipping area 120. The production system receives animals from a given lot 102A-k, where typically k is greater than or equal to 1. Animals received from a given lot 102 go through the pre-harvest area 104. Generally, in order to ensure a high quality of product, suppliers with supplier numbers are used. A supplier number registers that particular supplier and provides them with a lot number or supplier number. Typically, a qualified supplier complies with Environmental Protection Agency (EPA) and Concentrated Animal Feeding Operations (CAFO) regulations.

Animals arising at the pre-harvest area 104 from their respective lots 102 are assigned a lot number, corresponding to the lot which they were delivered with. Other information regarding the lot is also provided. For example, the number of animals in a particular lot 102, the sex of the animals in the lot 102, the feedlot of origin corresponding to the given lot 102, the day of slaughter, and other information may be recorded at the pre-harvest area 104. The production and tracking system 100 further comprises a central processor 124 comprising a tracking member 128 and a database 132. The determined information in the pre-harvest area 104 is sent to the central processor 124 via interface 136. The central processor then handles the information accordingly based on the required amount of information needed at any given step along the production process, and stores that information in a suitable format in database 132.

The interface 136 may be a bidirectional interface allowing communications to/from the central processor 124 and various components of the meat production system 100. Alternatively, the interface 136 may be a unidirectional interface that simply transfers information from any one of given areas to the central processor 124. In production, the animals are taken from the pre-harvest area 104 to the slaughter area 108 where they are slaughtered. In the slaughter area 108, the hide of the animal is removed from the carcass and the carcass in washed. The carcass may also be steamed pasteurized, receive a euhygenic bacteria treatment, and be subjected to an electrical stimulation process. In the slaughter area 108, carcasses are cross-referenced with animal ear tags otherwise known as a head tag system. This cross-referencing maps every carcass to an individual animal. Ear tag and head tag numbers are paired, collected, and recorded at the slaughter area 108. The information that is recorded in the slaughter area 108 is again sent to the central processor 124 where it is linked together, processed and then saved in database 132 in the appropriate format.

Also in the slaughter area 108, a carcass crosses a scale where it is weighed and assigned a unique carcass identification number. The carcass identification number references the animal number and the corresponding lot number. The unique carcass identification number may also contain additional data including the kill date, the processing shift, and the hot carcass weight per side. Typically an animal is split into two sides, and therefore two carcasses, each having its own unique carcass identification number, correspond to a single animal. As noted above, this unique carcass identification number is also sent from the slaughter area 108 to the central processor 124 for storage in the database 132, where it may be linked to additional information regarding the animal, such as a lot of origin.

After the animal has passed through the slaughter area 108, the corresponding carcass(es) are sent into the chilling area 112 where they are suitably chilled for a predetermined amount of time. After a carcass has been chilled for the requisite amount of time, it is sent into the fabrication area 116. Carcasses cross a transfer scale out of the chilling area 112 into the fabrication area 116 where they are weighed. The weight is logged at the transfer scale as the "chilled carcass weight" and sent to the central processor 124. Additional information including, but not limited to, the time of processing, the shift at which the carcass was processed at the transfer scale, animal identification number, and corresponding lot number may be saved and sent to central processor 124 for storage in the database 132 as well, where it may be linked to additional information regarding the animal, such as a lot of origin.

In the fabrication area 116 the carcass is separated into different parts. For example, one beef carcass may be split into a butt section, a chuck roll section, a strip section, a top round section, a bone-in-rib product, or any other suitable meat product that can be derived from the carcass. Each product class has a processing time associated with it, which takes into account quality assurance, ergonomic studies, time and travel across fabrication floor, and any other information that can be used to determine the amount of time it takes to produce the produce in the fabrication area 116. This processing time typically corresponds to a window of traceability 300, as will be described in further detail later. Each window of traceability 300 can be traced to a carcass identification number, lot number, and feed lot of origin. This window of traceability 300 may be saved in the database by transferring the information from the fabrication area 116 to the central processor 124 where it is saved in the database 132.

Once the carcass has been properly processed into a final product, it is sent from the fabrication area to the packaging and shipping area 120. In the packaging and shipping area 120 each box containing products is labeled with information. The box information may include product code corresponding to the type of product that is within the box, product serial number, time of production, production shift, and/or destination. The final boxed or packaged product is then sent from the packaging and shipping area 120 to either a retailer or an end customer.

Figure 2:
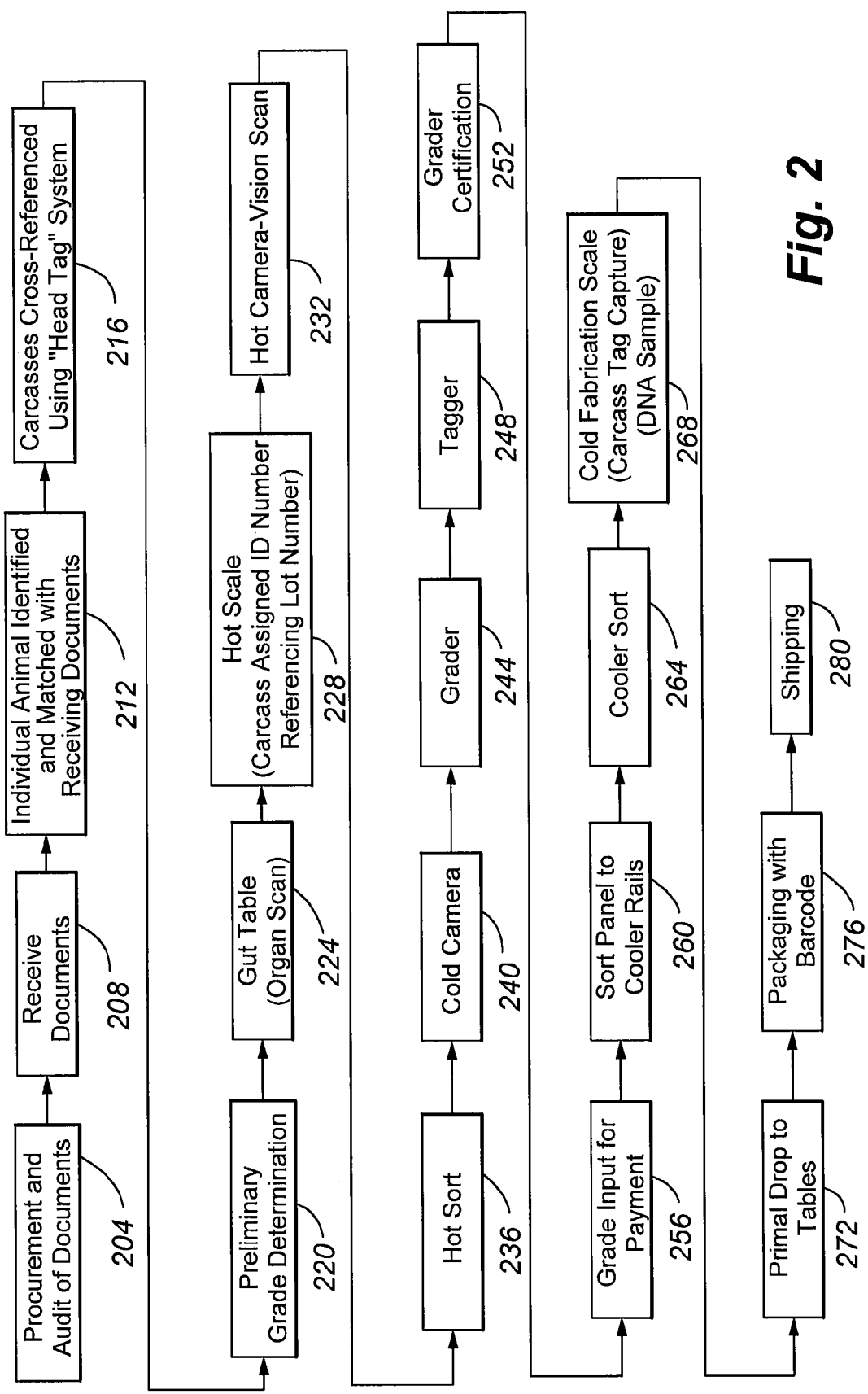
FIG. 2 is a block diagram depicting a general production and tracking process in accordance with at least some embodiments of the present invention.

Referring now to FIG. 2, a more detailed description of the production and tracking process will be described in accordance with embodiments of the present invention. In step 204, documents relating to a lot and/or animal associated with a particular lot are procured at the pre-harvest area 104. In this regard, but not portending to be limited in any manner, the following U.S. patents are incorporated herein by reference to assist in providing a written description of how one of skill in the art may implement one or more embodiments of the present invention: U.S. Pat. No. 5,478,990 to Montanari et al. and U.S. Pat. No. 6,975,223 to Grose et al. Procurement and audit of documents may include vision supply base, future supply projections, information supplier's data, and other relevant supplier information. The received documents are generally used to verify the age of incoming animals, the source of these animals, and may include a determination as to whether the animals are organic and natural (i.e., have not been exposed to chemicals or other additives) in addition to other items of interest with respect to the animals (step 208). In step 212, each individual animal is identified and matched with receiving documents. For example, if fifty animals were received in a particular lot 102, then each animal is matched to that particular lot 102. The animal records are gathered, the animal identification number is recorded, and both are then sent to central processor 124. The animal may also undergo an optibrand vision scan which matches the receiving documents of the lot to that animal. Thereafter, the animal is sent from the pre-harvest area 104 to the slaughter area 108 as described above.

In the slaughter area 108 a carcass is cross-referenced to the animal and lot it came from using a head tag system linking the individual animal's identification number to the lot number (step 216). Thereafter, a determination of grade (such as Angus) and/or breed is made and if applicable, the carcass is stamped as having a high grade of meat (step 220). In step 224, the carcass is sent to the gut table where the animal's organs, as well as the physiological structures in which they are contained, are analyzed to make an initial determination of the health of the animal. Typically, a viscera loss report is generated at the gut table, which will contain information regarding this initial determination. If, during the viscera test, it is determined that the animal's health is questionable, then all carcasses associated with that animal are recalled and tested further to ensure the quality of the meat. By way of example, and while riot wishing to be limited in any manner, pork lungs that are infected by *Pasteurella multocida* and/or *Actinobacillus pleuropneumoniea* may contain lesions that cause the lungs to adhere to the inside of the rib cage, thereby damaging the lungs when the lungs are removed. This adhesion is indicative of respiratory complications in the animal and is a visual means of identifying an animal of lesser quality. Additionally, the livers from cattle that have experienced complications, such as pathogenic bacterial infection, from a fast conversion to a high protein diet may contain abscesses, which are also indicative of the overall health of the animal. The existence of these maladies, among others, may be determined visually at the gut table, by hand or human inspection, or by use of the systems and methods of the present invention, as described below.

At the gut table 224, an additional step may be performed where one or more organs of the given carcass are scanned by the systems of the present invention. When the organs are removed from the carcass, they are typically placed on a conveyer belt, or similar means of transport, along with the carcass they were removed from. As can be seen in FIG. 5, the conveyor belt 500 is generally divided into a first section 504 and a second section 508. Organs on the belt 500 are generally separated such that an organ of interest 512 is placed on the first section 504 and the other viscera 516 are placed on the second section 508. The organ, placed onto the first section 504 of the belt 500, travels in the general direction of arrow 518. As the organ moves with the belt it is passed under an optical instrument capable of generating an image of the organ 520, such as still images or sequences of moving images. This image generation means 520 is arranged such that an image is generated of any organ that passes through an area of interest 522 underneath the image generation means 520, and may be equipped with a motion detector or the like that helps to automatically detect the presence of an organ in the area of interest 522. The image gathering means 520 may be one of many items capable of creating an image, photographic or otherwise, of the organ as it passes underneath, such as a camera (film or digital; color or black and white), a video camera (film or digital; color or black and white), an Internet-operable web camera, an x-ray device, calorimeter, fiberscope, optrode, infrared sensor (passive or otherwise), photodetector, photometer, telescope, videoscope, and/or any similar device as well as any combination of the foregoing. In the presently preferred embodiment, the image gathering means 520 is a camera, more preferably a digital color camera. The image gathering means 520 may thus be fixedly located above, alongside, or beneath the conveyer belt 500, it may also be rotatably mounted such that it is movable between each such position as well as any position in between, or it may be present near the conveyer belt 500 such that an attendant may manually use the image gathering means 520 to generate images of the organ of interest. The image gathering means 520 may also be equipped with a motion detector or the like that helps to automatically detect the presence of an organ in the area of interest 522 so that it may operate without the assistance of an attendant.

Once the organ is within the area of interest 522, the image gathering means 520 generates or otherwise obtains at least one image of the organ, which is then sent to the processor 124. The processor 124 determines what animal and/or lot the organ is associated with and creates a data pointer between the subject image of the organ and the animal/lot that the organ is associated with. The data pointer may be a memory address of the data for the animal/lot. The processor 124 may alternatively stamp the image with the corresponding animal/lot identification number/name such that anyone that looks at the image knows what animal the organ came from and subsequently what lot the animal originated from. The processor 124 then sends the image to the database 132 for storage.

Referring now to FIGS. 6A-C exemplary images captured by the image gathering means 520 will be discussed in accordance with at least some embodiments of the present invention. The organ of interest 512 shown in FIG. 6A, an image of which has been generated by the image gathering means 520 as it passed through the area of interest 522, has no visible abnormalities. The organ therefore appears to be healthy and, as such, has been given one stamp 604 as an indication that the organ is healthy. In the United States, a USDA employee stands at the belt 500 and grades each organ that may be consumed by humans and/or animals. The grader is responsible for assigning each organ a grade based on its appearance. An organ that appears healthy to the inspector is typically given one USDA stamp, which signifies a healthy organ and a favorable grade. When the processor 124 receives the image of FIG. 6A, the processor 124 may use standard image processing techniques to determine that the organ was given only one stamp, in addition to storing the image of the single stamp given. The image shown in FIG. 6B has a few abnormalities 608, which may be abscesses, tissue damage, or other maladies, and thus has been given a grade of two stamps 604, indicating that the organ is safe for animal consumption but not for human consumption. The presence of these abnormalities may be an indicator to the rancher who supplied the animal, or to a company that supplied drugs to the rancher, that something is wrong either with the animal or the animal's diet. For example, the presence of a large number of abnormalities may indicate, among other things, that the rancher did not use a drug or combination of drugs to improve the animal's health in advance of slaughter, which may have reduced or eliminated the abnormalities 608 in the organ. The image shown in FIG. 6C has a number of abnormalities 608 and as a result has been given three stamps 604, indicating that the organ is not safe for human or animal consumption and must be removed from production and destroyed.

There are a number of ways to indicate the grade that a particular organ has received. As discussed above, one scheme for indicating the grade of a particular organ corresponds to how many stamps the organ receives. The more stamps the organ has received, the lesser the quality of the organ. As can be appreciated by one of skill in the art, under different circumstances and/or inspection schemes, the presence of multiple stamps on an organ may indicate that the organ is of higher quality than an organ with fewer stamps. In each case, however, the grade can be readily determined using the systems and methods of the present invention, as noted above.

The images of the organs are sent to the central processor 124 where they are analyzed. Typically the processor 124 searches for and counts the number of stamps 604 that appear in the image and registers the grade of the organ 512 based on the number of stamps 604 present. Alternatively, the processor 124 may not rely on stamps 604 and could instead directly count the number of abnormalities 608 that exist on the organ 512. Using certain image processing techniques, the values of the pixels associated with the stamps and/or the abnormalities could be counted and if the number of those pixels (which may be, for example, pixels that have a different color than their surrounding pixels) exceeds a certain threshold, then the quality of the organ can be downgraded. In order to identify abnormalities and/or the stamps applied by the grader, the processor 124 is operable to scan the image and determine the value of each pixel. Typically, a darker pixel is given a higher intensity value and a lighter pixel is given a lower intensity score. The processor 124 compares the intensity values of each pixel and those immediately next to the pixel. When the processor 124 identifies a pixel that has one or more pixels next to it with a substantially different intensity value, then the processor 124 marks that pixel as a potential abnormality and/or stamp. The processor 124 then tries to determine if a number of marked pixels are in a group. If there are a number of marked pixels in a group, then the processor 124 can mark the group as a potential abnormality and/or a stamp. The size and shape of the group is analyzed to further determine whether the group is an abnormality or a stamp. The number of abnormalities or stamps are then counted to determine what grade the organ was given or what grade it may be given. Once the processor 124 determines the grade then the grade is associated with the lot and/or animal that the organ originated from. This valuable information may be stored in the database 132 and sent to the supplier of the lot for analysis of the quality of the lot.

During the organ scan (step 224) an image gathering means 520 is used to scan each organ as it passes the gut table. By scanning the organ with an image gathering means 520, organ abnormalities may be identified. If too many abnormalities are discovered on a single organ, the carcass(es) associated with that organ may be recalled immediately, prior to any additional production on that meat, as many organs are useful indicators of an animal's overall health and the carcasses associated with such organ may similarly be of low grade or quality. Some or many organ abnormalities may indicate that the animal was not a healthy animal and therefore may not be able to meet suitable quality standards. If, during organ scanning, it is determined that the animal was unhealthy, the carcasses associated with that organ are recalled and further quality testing is performed to ensure that the carcasses are suitable for consumption.

Figure 7:
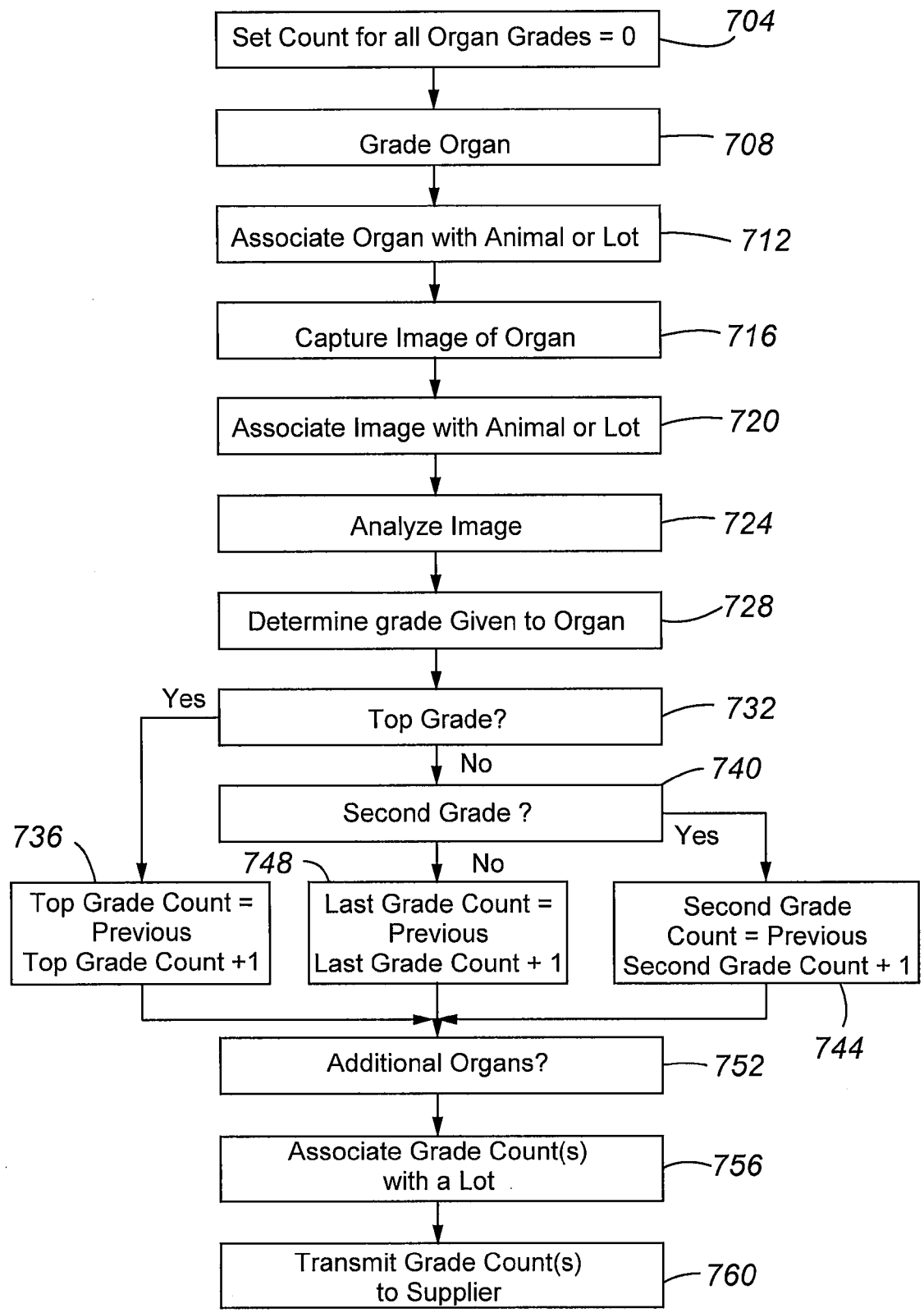
FIG. 7 depicts a method of tracking and accounting organ quality in accordance with at least some embodiments of the present invention.

Referring to FIG. 7 a method of scanning organs of interest 512 during meat production will be described in accordance with at least some embodiments of the present invention. Initially, a count variable for all of the organ grades is set to zero (step 704). Thereafter, a first organ is graded by either manual or automatic methods (step 708). The graded organ is then associated with an animal/lot (step 712). By associating an organ with an animal and/or lot, information already stored in the database 132 regarding that animal/lot can be logically connected with the organ such that any additional information that is determined about the organ can also be stored with the animal/lot information in the database 132.

As the organ 512 passes into the area of interest, an image of the organ 512 is captured by the image gathering means 520 (step 716). The image is transmitted to the processor 124 and associated (e.g., stored in the database with images of other organs from the same animal/lot or stamped with animal/lot information) with an animal/lot (step 720). Then in step 724 the processor 124 analyzes the image to how many, and possibly what kind of, markings, abnormalities, and/or stamps exist on the organ 512. Based on this analysis, the grade of the organ 512 is determined by processor 124 and stored with the rest of the pertinent information relating to image and/or the animal/lot associated with the image (step 728).

In step 732, it is determined whether the organ 512 was given the top grade. In the event that the organ 512 has received a top grade, then the variable corresponding to the top grade count for a given lot is incremented by one from its previous value, which would be zero for the first organ (step 736). However, if the organ 512 was not given the top grade then it is determined if the organ 512 was given the second highest grade (step 740). If the organ 512 was given the second highest grade, then the variable corresponding to the second highest grade count is incremented by one from its previous value (step 744). If the organ was not given the second highest grade then the lowest grade count is incremented by one from its previous value (step 748). For purposes of illustration only three grades have been described, but it is possible to implement embodiments of the present invention where numerous grades exist for a particular organ. Each grade would have a corresponding variable dedicated to keeping track of the number of organs that have received that grade. Once the variable associated with the grade of the organ has been incremented, it is determined if there are any additional organs that need to be analyzed (step 752). If there are more organs that have to be scanned, then the method returns to step 708.

Once a suitable number of organs have been analyzed (e.g., all of the organs from animals corresponding to a particular lot of origin), then the grade counts of each variable are associated with a lot (step 756). In a preferred embodiment, when an organ associated with a new lot is scanned, then the value for each variable of each grade count is stored with other lot information and the variables are reset to begin counting for the new lot. After a suitable number of organs have been scanned and the grade counts of the scanned organs are stored along with the other lot information, a report containing the grade counts and any other pertinent information may be generated by the systems of the present invention. This report may then be forwarded to the supplier of the lot (step 760), for a fee or otherwise. This provides easily verifiable and accurate feedback to the lot supplier about the quality of his/her lot. Additionally, the report can be sent to other entities. For example, the report may be transmitted to a drug company that supplies ranchers with drugs or combinations of drugs that is supposed to increase the health of animals delivered for slaughter. By viewing the report, the drug company will be able to determine whether the lot supplier used any of their drugs and/or whether the drugs sold to a certain lot supplier proved to be efficacious, provided that such drugs elicit effects capable of being captured by the image gathering means 520. For example, if the report shows that a particular lot supplier, who purchased one or more drugs from the drug company, provided a large number of high quality organs, then the drug company can use the report as proof of the drug's efficacy and can therefore attempt to charge a premium for it. As can be appreciated, the information from scanning organs of interest 512 may be valuable to a number of other entities involved in the meat production supply chain.

Figure 8:
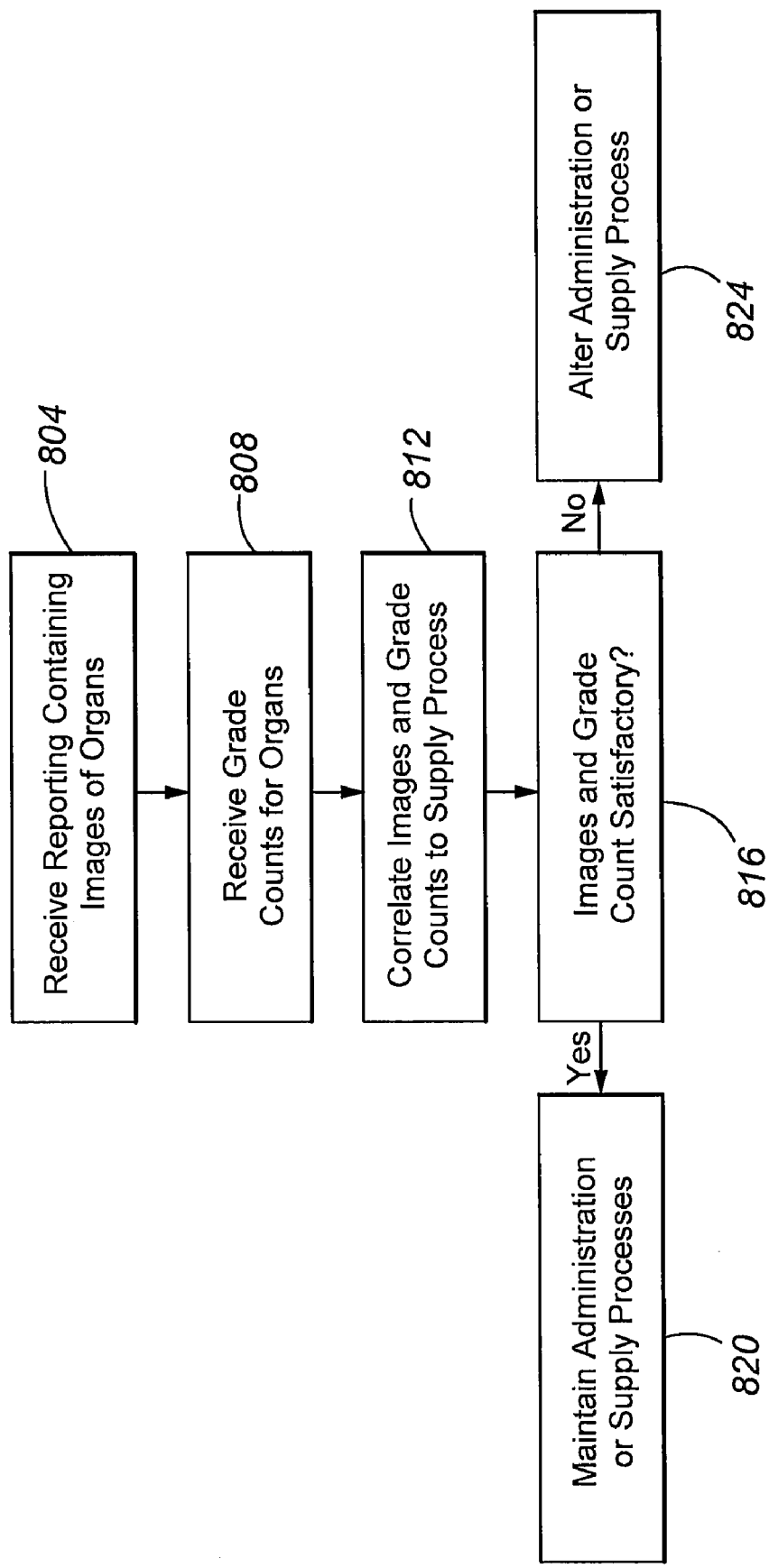
FIG. 8 depicts a method of utilizing accounting information in accordance with at least some embodiments of the present invention.

Referring now to FIG. 8 a method of utilizing information supplied from the organ scanning method will be described in accordance with at least some embodiments of the present invention. Initially, a report containing images of the organs and other information related to a lot of origin (e.g., number of animals in the lot, overall quality of the lot, price paid for the lot, price paid per head of animal, time of day lot was processed, lot number, and so on) are transmitted to the supplier (step 804), for a fee or otherwise. The report may also include a description of the grade of the organ, the associated lot number and corresponding animal number, as well as the grade counts for the organs (step 808). The grade counts may correspond to the number of organs that had a particular grade score. For example, a given lot may have had a large number of organs with a top quality grade, a moderate number of organs with a second quality grade, and a small number of organs with the lowest quality grade. By having the report, the supplier is able to correlate the images of the organs to the grade counts, to verify the accuracy of the grade counts (step 812).

Based on the feedback received by both the images and the grade count for each image, the supplier can determine how best to proceed with raising animals. In step 816, it is determined if the images and grade count correspond to a satisfactory level. For instance, if the number of lowest quality grades received is larger than a predetermined satisfactory level of the entire lot, then the lot may not have been raised to a satisfactory level. In the event that the lot did meet the minimum requirements, then the supplier may decide to maintain his/her process (step 820). However, if the feedback shows that the supplier is raising lower quality animals, then the supplier may decide to alter the manner in which they raise their cattle (step 824). For example, if they supplier had not previously been purchasing drugs or combinations of drugs designed to increase the overall health of his or her animals in advance of slaughter, then the supplier may choose to begin purchasing the same. Additionally, the information can be provided directly to the drug company, for a fee or otherwise, so that they can determine if their product is working effectively. If the drugs or combinations of drugs are working effectively, then the drug company may be able to ask a premium for their drugs or combinations of drugs. Conversely, if the feedback indicates that their product does not work, then the drug company may need to redesign their particular product.

Referring back to FIG. 2, after the organ has been scanned and other necessary tests have been performed, the carcass and/or organ is sent to a hot scale (step 228). At the hot scale, each carcass and/or organ is given a unique identification number linked to the head tag. This references the lot number, contains additional data including the kill date processing shift, hot carcass and/or organ weight per side and so on. That information is then transferred to the central processor 124 for storage in the database 132. Thereafter (step 232), each carcass and/or organ is analyzed with another image gathering means, such as a hot camera, that enables the user to make an initial determination or prediction of its quality. Thereafter the carcass and/or organ is sent to the hot sort in step 236.

Once the slaughter process has been completed, the carcass and/or organ is sent into the chilling area 112 where initially yet another image gathering means, such as a cold camera, is used to determine the appearance, size of the rib-eye, color, fat cover and marbling of each carcass (step 240). This information is used by a grader to determine yield grade, quality grade and so on (step 244). Thereafter, the tagger tags the carcass and/or organ and captures data related to that carcass and/or organ (step 248). That data may include data that was recovered from this image gathering means, the grader or any other previously performed step. The information is then sent to the central processor 124 for storage in the database 132.

In step 252, a grader certification is performed meaning that the original grade is confirmed by a second party. In step 256, grade input for payment is performed. This typically involves determining the actual amount of money that may be received for the given grade. The carcass and/or organ is then sent to a sort panel to be stored on cooler rails in step 260. Thereafter, the carcass and/or organ is sorted and stored in a cooler for a predetermined amount of time in step 264. During cooler sort, the location of the carcass and/or organ is known and may be tied to any of the previously mentioned information. This enables the production facility to quickly locate the carcass and/or organ in the cooler if it is determined that the given carcass and/or organ needs to be recalled and/or retrieved for any purpose.

After the carcass and/or organ has stayed in the cooler for a predetermined amount of time, the carcass and/or organ is sent from the chilling area 112 to the fabrication area 116. As the carcass and/or organ passes between the chilling area 112 and the fabrication area 116, it is weighed at a cold fabrication scale (step 268). At the cold fabrication scale, the carcass and/or organ tag information is captured and stored and sent to the central processor 124 and stored in the database 132. Additionally, a DNA sample may be taken from the carcass and/or organ as it passes across the cold fabrication scale. This may ensure a higher level of accuracy in determining and tracing the origins of a carcass and/or organ. Thereafter, a primal drop of two tables is performed in step 272. Each product may be sorted and produced according to known methods.

Figure 3:
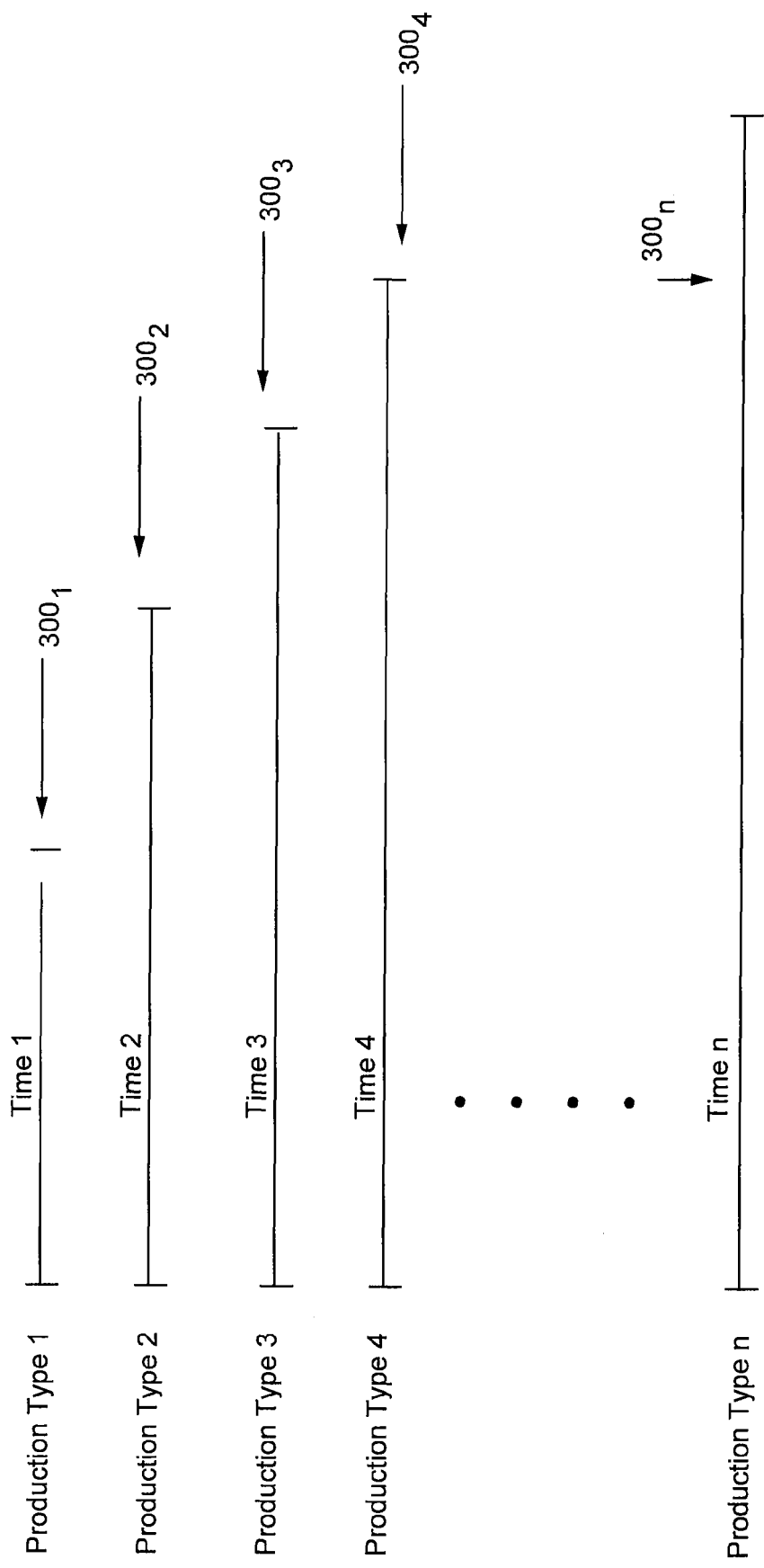
FIG. 3 is a depiction of various processing time windows of traceability in accordance with at least some embodiments of the present invention.

Referring now to FIG. 3, an explanation of the different types of products and the amount of time required to produce such products will be discussed in accordance with embodiments of the present invention. Because the fabrication process is a known process, it is possible to create a window of traceability 300 that allows each product to be accurately traced though the fabrication process. For example, properly removing an intact liver from a beef carcass may typically correlate to a product type called "type 1," which is a product that takes approximately 17 minutes to remove from the carcass. This results in a first window of traceability 300.sub.1 equaling approximately 17 minutes for a type 1 product. Another product may take a longer amount of time to produce and would therefore correlate to a different product type having a different length of time needed for it to be properly processed. For example, a product of type 4 may correspond to the processing of pork ribs, including the removal of the lungs from the pleural cavities. Based on ergonomic studies and known fabrication methods, it may be determined that a fourth window of traceability 300.sub.4, corresponding to product type 4, is approximately 18.5 minutes. This way, each window of traceability 300 may correspond to a different product or part of the slaughter process. Each time a window of traceability 300 is determined, it can be traced to a carcass' ID, lot number, and ultimately feedlot of origin. There may be any number of traceability windows 300 in a given fabrication process, and each may, though it is not required, correspond to a different product.

Referring back to FIG. 2, once each product has been produced, it is sent to the packaging and shipping area 120 where it is packaged with a packaging bar code (step 276). Packaging may include individually packaging each product or grouping a number of products together into a box, for example, such that the box contains a number of carcasses and/or organs. One box may correspond to four or five different carcasses and/or organs and each carcass and/or organ is not necessarily associated with the same animal. However, the information printed on the box may include the product code or the type of products that are packaged within, together with the serial number of the box, time of packaging of the box and the production shift in which it was packaged. Again this information is sent to the central processor 124 and saved in the database 132. Once the packages have been properly labeled, they are shipped to the end customer (step 280).

Figure 4:
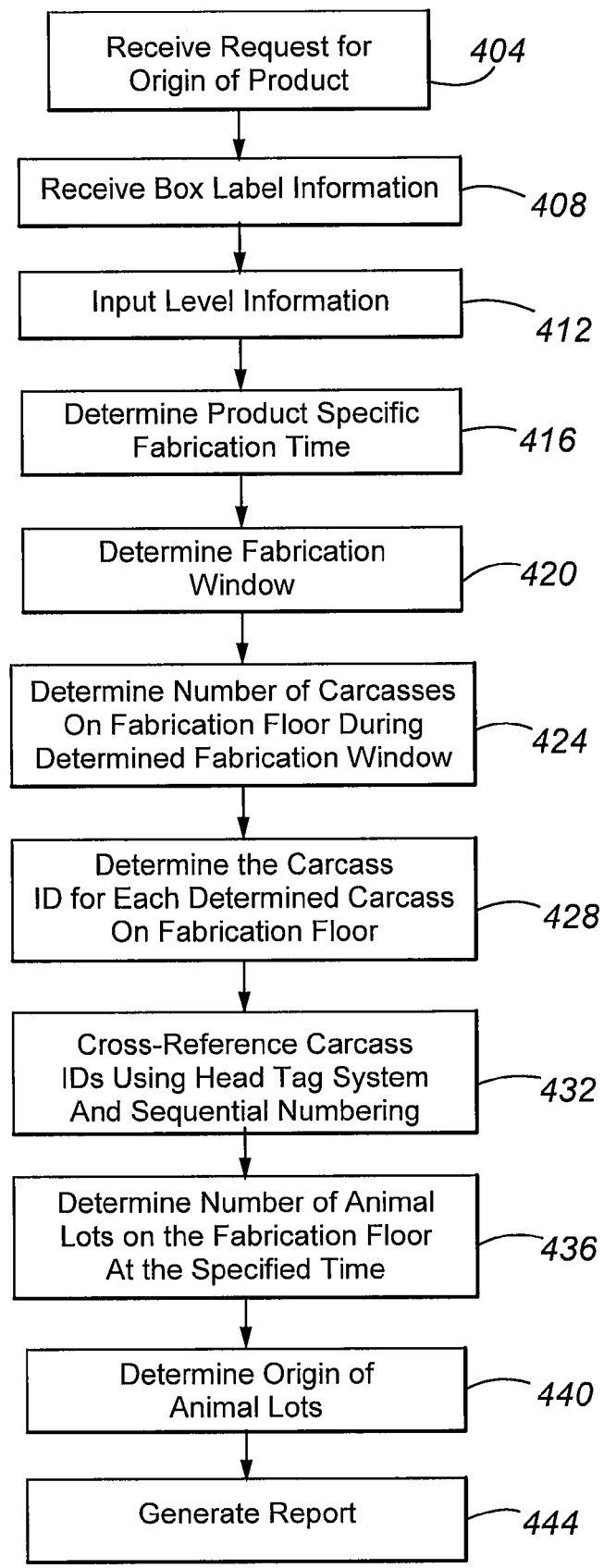
FIG. 4 shows a method of determining the origin of end products in accordance with at least some embodiments of the present invention.

Referring now to FIG. 4, a method of tracing an end product, and preferably an organ, back to its origin will be described in accordance with embodiments of the present invention. Initially, in step 404, a request to determine the origin of a product is received at the tracking member 128, at which time the requestor provides the box label information, such as the bar code applied in step 276 of FIG. 2, which is received by the central processor 124 in step 408. Such box information may include, without limitation, the box serial number, product code, time of production/packaging of the box, and the production shift in which the product was packaged. Upon receipt of the request, the box label information may be input into the tracking member 128, as in step 412, though the information may also be input directly to the central processor 124 or at a remote terminal that can communicate with the central processor 124 and/or the database 132. Once the label information is input, the product specific fabrication time is determined in step 416. Using the product specific fabrication time, a corresponding fabrication window or window of traceability 300 is determined in step 420. The window of traceability 300 may be used to help determine the number of carcasses and/or organs that were on the fabrication floor during the determined fabrication window (step 424).

Once the number of carcasses and/or organs on the fabrication floor during a given window of traceability 300 is determined, the tracking member 128 is able to determine the carcass ID for each carcass and/or organ determined to be on the fabrication floor in step 428, utilizing information from the database 132 (step 428). The tracking member 128 may then cross-reference the carcass IDs using the head tag system. The cross-referencing performed by the tracking member 128 in step 432 then allows the number of animal lots to be determined in step 436. Specifically, the tracking member 128 determines the number of animal lots on the fabrication floor during the determined window of traceability 300. That information can then be used to determine the origin of each of those animal lots in step 440. Based on this information, the tracking member 128 may then be able to generate a report for the requester of the origin information (step 444). The report may include, but is not limited to, the carcass ID, lot identification number, kill date, fabrication time, number of potential carcasses in the box, number of potential animals in the box, potential member of kill lots in the box, and the corresponding animal feed lot of each kill lot. This information is generally based on the window of traceability 300 and the corresponding information that was stored in the database 132.

The management and tracking system 100 of the present invention allows for backwards and forwards tracking of a carcass, organ and/or animal from any point during the production, fabrication and consumption process. Using embodiments of the present invention, any carcass, organ and/or animal may be recalled or withdrawn within a time frame of about two hours during the production process. The data management and tracking system 100 may also be used to produce reports and sell data back to producers by lot and/or by individual animals within that lot. Also various steps, for example, the organ-scanning step, may be correlated with other steps and information related to that test is maintained in the database 132 along with the corresponding carcass/animal. That data may be sold back to animal health suppliers to allow them to determine how certain animals and/or lots are affected by a particular type of treatment for organs and/or any other health concerns.

The system is also compliant with USDA and FDA regulations therefore making it safe and reliable to the consumers. The process may also improve the sorting efficiency rate of the carcass which in turn leads to subprimal maximization. Additionally, because the window of traceability 300 can be determined throughout the production process, information relating to the fabrication of a given product type does not necessarily need to be stored in the database 132 for each carcass. This makes it easier to maintain a database 132 and track carcasses during the fabrication and production process.

Figure 9:
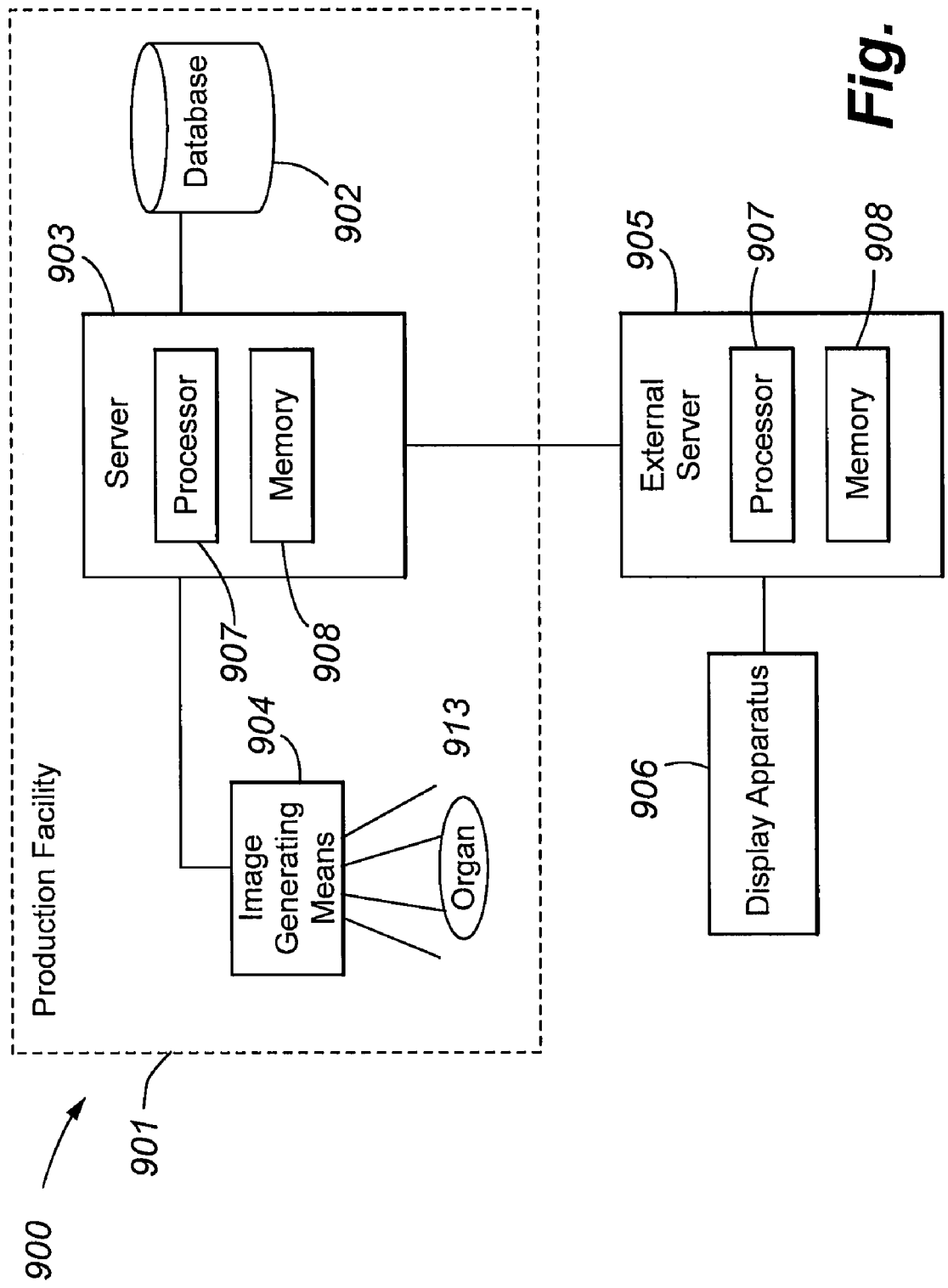
FIG. 9 is a block diagram of components of a meat production and tracking system in accordance with at least some embodiments of the present invention.

Referring now to FIG. 9, a system 900 for administering a drug program related to livestock is described in accordance with certain embodiments of the present invention. The system 900 generally comprises a meat production facility 901, which contains a number of production areas (not shown), a database 902, a server 903, at least one image gathering means 904, at least one external server 905, and at least one display apparatus 906. While the discussion presented below with respect to the image gathering means 904, at least one external server 905 and at least one display apparatus 906 refers to each structure singularly, it should be recognized, and it is intended, that a plurality of these features may exist and operate as a part of one or more embodiments of the present invention.

The server 903 and the external server 905 further comprise a processor 907 and memory 908, in addition to the internal circuitry, software and components typically associated with computer servers (not shown). The image gathering means 904 is operably and functionally connected to the server 903, via standard means, such that information may be freely transmitted in both directions between the image gathering means 904 and the server 903, or in a single direction only. Similarly, the database 902 is operably and functionally connected to the server 903, via standard means, such that information can be freely transmitted in both directions between the database 902 and the server 903, or in a single direction only. As can be appreciated, while the external server 905 is also operably and functionally connected to the server 903 via standard means, such that information may be freely transmitted between the external server 905 and the server 903, it may be desirable to configure this interconnection such that the flow of information may be limited to delivery of information from the server 903 to the external server 905, but not vice versa.

In operation, the system 900 functions substantially as described below. A livestock breeder will typically deliver livestock to the meat production facility 901 for slaughter. Upon receipt of such livestock, data concerning the livestock delivered and the delivering breeder is typically obtained, as previously described. This data may include, without limitation, the date and time of delivery, the specific lot number or numbers of livestock delivered, the number of animals delivered, the sex of each of the animals, the ear tag numbers of each animal, if any, the anticipated date and time of slaughter, the name and address of the breeder, the type(s) of livestock bred by that breeder, whether that breeder indicates that the livestock delivered have been given one or more drugs to increase their health in advance of slaughter, what types and/or brand names of drugs had been given, if any, and similar information. Once this information is obtained, it is input into the server 903. Each item of information is then linked together by the server 903 and stored and/or archived in the database 902 as a packet of linked information, or the server 903 may tag or identify each item of information with an electronic signature or data pointer so that each item may be stored and/or archived in the database 902 individually in a form that is readable by the server 903 and that can be readily linked, associated or joined with other data points by the server 903 at a future point in time.

As each delivered animal is slaughtered, it is broken down into a plurality of carcasses and meat products, which will travel between production areas in the production facility 901 where they will be processed into their final form and packaged for sale. Carcasses and meat products typically move through the meat production facility 901 via mechanical means of transport known to those of skill in the art, such as conveyer belts, hooks, wheeled carts, or similar means of transport. The image gathering means 904 may be located at any number of locations within the meat production facility 901, but is preferably located over, under, and/or adjacent to the transport means so that a carcass or meat product, and preferably an organ 913, may travel within close proximity to the image gathering means 904 as it moves from one location in the production facility 901 to another. This way, a carcass or meat product, and preferably an organ 913, may pass within the field of view of the image gathering means 904, allowing the image gathering means 904 to generate one or more images of it automatically, or may pass within reach of an operator who may then manually place the image gathering means 904 in an optimal position to generate one or more images. Once an image has been generated, the image gathering means 904 transmits the image electronically to the server 903 where it is tagged or identified by the server 903 with an electronic signature or data pointer, thus enabling it to be linked with other information already present and/or archived in the database 902 containing a related tag or identifier and stored as a part of a discreet packet of linked information, and/or stored or archived in the database 902 as an individual item of information that can be readily linked with other data points at a future point in time. Thereafter, the image may be transmitted outside of the production facility

901 to an external server 905 as a single item of data or as part of a series of linked information, where it may be visualized on a display apparatus 906 as an image and/or part of a data report.

By way of example, and without wishing to be limited in any manner, consider that, after an animal has been humanely dispatched, it is subjected to a washing procedure inside of the production facility 901. One or more image gathering means 904 may be present in the washing area of the production facility 901 so that it may generate an image of the animal as it is being washed. This image, which may be tagged with the time the image was generated by the image gathering means 904 itself, is then sent to the server 903 where it is tagged or identified with an electronic signature or data pointer so as to allow it to be linked directly to the information gathered about the animal as it was brought in, as discussed above. Since the image of the washed animal will be obtained shortly after delivery of the animal in question, it will be possible for the server 903 to associate the image of the animal generated during washing with certain identifying data for the animal gathered at intake, such as an ear tag number and lot of origin, that already exist as stored and/or archived information in the database 902. Therefore, in linked form, this image may be used to ultimately trace the animal, in the form it exists as it is being washed, to a head tag number, lot of origin and ultimately to the breeder that delivered the animal for slaughter, in addition to all of the other information obtained at intake.

This process may continue for each successive step in the production process, which are described above, such that images may be generated by a image gathering means 904 at numerous locations along the production line and each linked to the information regarding the production step that preceded it. Thus, when an image of a carcass or meat product, and preferably an organ 913, is obtained by the image gathering means 904, it may be linked to one or more images obtained at the immediately preceding step in the production process, and ultimately traced backward such that the image of the carcass or meat product, and preferably an organ 913, can be directly linked to information concerning the breeder, whether that breeder indicated that a drug had been administered in advance of slaughter, the sex and weight of the animal at the time of delivery, and similar information. This information, which is being gathered and linked electronically, allows the production facility 901 to receive and analyze information concerning a single animal as it is being processed, in near real-time.

The image gathering means 904 will preferably be located over the transport means such that it can generate an image of a carcass or meat product, and preferably an organ 913, from above, though it may also be located under or adjacent to the transport means and/or mounted on a mobile apparatus such that its position may be moved between each of these positions as well as any position in between. This way, a carcass or meat product, and preferably an organ 913, may pass within the field of view of the image gathering means 904, allowing the image gathering means 904 to generate one or more images of it automatically, or may pass within reach of an operator who may then manually place the image gathering means 904 in an optimal position to generate one or more images. The use of a transparent means of transport is contemplated for the present invention, to allow the image gathering means 904 to be able to generate images of an item of interest from underneath the transport means. The entirety of the transport means may be transparent or it may be transparent in sections. Preferably, the image gathering means 904 will be located along the meat production line immediately after a location where a stamped determination of grade or quality is made on a carcass or meat product, and preferably an organ 913, so that the image gathering means 904 can generate one or more images depicting, and therefore evidencing, the grade or quality given at the earliest possible time.

In one embodiment, the image gathering means 904 is programmed to generate images automatically and contains software that enables it to determine when an item passing by it on the transport means is centered in its field of view. Such software may be one of many types known to those of skill in the art, but may include color recognition software that recognizes the difference in color between the transport means and the item to be imaged that has been placed on the transport means, as well as heat recognition software that is operable to detect the difference in temperature between the transport means and the item to be captured in one or more images. The image gathering means 904 will also be operable to determine when it has generated an image of an item that is centered and in focus from an image that is out of focus, where the item to be imaged is fully or partially blocked from the field of view of the image gathering means 904, where the item to be imaged is not centered, and/or that has similar troubles. The image gathering means 904 will thus be operable to alert the production facility 901 as to the failure, so that the item to be imaged can be re-imaged and/or manually investigated. Such an alert may be of many means, ranging from an electronic alert sent to the server 903 to an audible alarm that will sound in the production area where the image gathering means 904 is located to alert the production facility 901 that the image gathering means 904 failed to obtain or generate an acceptable image. This difficulty may also be overcome by the presence of more than one image gathering means 904 in succession along the transport means, whereby a successive image gathering means 904 may generate an acceptable image of the item that was not successfully imaged by a previous image gathering means 904.

The software of the image gathering means 904 will also enable it to distinguish between slight differences in color in an item to be imaged and to zoom in on a particular area that may be of interest to generate a magnified image of a specific area of the item in question. The image gathering means 904 is thus able to distinguish between the native color of the item in question and any colored aberrations or foreign objects that may exist on such an item, but utilizing color recognition software as described above. By way of example, and without desiring to be limited in any manner, consider a beef liver that has been inspected by the USDA and given a grade via the application of one or more stamps. The image gathering means 904 will be able to distinguish between the natural color of the beef liver and the color of the USDA stamp such that it may zoom in on the stamp to obtain a close-up image of it. The image gathering means 904 will also be able to distinguish between the color of an abnormality on an organ and the natural color of the organ itself, thereby enabling it to zoom in on an abnormality and generate a magnified image of it. Once the image gathering means 904 determines that an acceptable image of the item in question has been generated, it transmits the image electronically to the server 903, as described above.

Because the system 900 is fully automated, it is possible for the server 903 to create reports containing packets of linked data concerning the slaughter and meat production statistics of an individual animal, or a group of animals, while that animal, or those animals, are still in the production facility 901. Therefore, the quality and health of an animal, or group of animals, as determined by the quality and grading stamps given to the carcasses, meat products and/or organs 913 derived from such animals, can be tracked and linked to a variety of related information, in near real-time. For example, the grade given to an organ can be ascertained by the image gathering means 904 and sent to the server 903 where it may be linked to information about the breeder that raised the animal from which the organ was derived as well as information as to whether that animal had been given a drug to increase its health in advance of slaughter. It is also possible for the server 903 to generate reports that link information about a specific breeder with images obtained as described herein, evidencing the quality and/or grading actually given to the animals delivered to the production facility 901 by that breeder over a certain period of time, thus revealing historical trends about the actual quality and grade of the animals raised by that breeder. It is also possible for the server 903 to generate reports that show linked data concerning, for example, all of the organs processed by the production facility 901 over a specified period of time, the grading each organ received, and the source of the animals from which the organs were derived. The server 903 can also generate reports linking information regarding the quality and/or grade given to specific carcasses, meat products or organs 913 with information as to whether the animals those carcasses, meat products or organs 913 were derived from had been given a drug to increase their health in advance of slaughter. Further, the server 903 can generate reports linking information showing the quality or grade actually given to an animal, or to a group of animals, with the administration of one or more specific types, or brand names, of drugs in advance of slaughter. As can be appreciated, it is possible for the server 903 to generate many different types of reports beyond and in addition to the examples provided above, as there are numerous ways in which the information gathered by the system 900 may be combined. Preferably, the reports generated by the server 903 will contain, at a minimum, information linking the health, quality or grade of an organ to the administration, or lack of administration, of a drug to an animal in advance of slaughter. The production facility 901 may elect to utilize the reports generated as a commodity, by selling the reports generated on a pre-request basis, a pre-purchased basis, a line-item basis, a per-request basis, an ongoing basis over a specified period of time (e.g. monthly, weekly, etc.), or by any number of other commercially viable means.

These types of reports, consisting of linked information created by the server 903, can be stored and/or archived in the database 902 or transmitted to an external server 905 that is operable to receive such information and viewed on a suitable display apparatus 906, such as a television or computer monitor. It will thus be possible for the production facility 901 to generate a variety of reports of linked information related to its daily operations and to store and/or archive those reports in the database 902 on a long term basis for future use. It is also possible for an entity other than the production facility 901, that has access to an external server 905 capable of receiving reports of linked information generated by the server 903, to receive such reports and to view them on a suitable display apparatus 906. Additionally, one of the objects of the present invention is for the server 903 to provide reports of linked information to an external server 905 in a secured format, such as read-only, whereby neither the recipient of the linked information, nor the external server 905, is capable of modifying or altering the report. This way, the production facility 901 can utilize the server 903 to generate and deliver reports to an external display apparatus 906, via an external server 905, such that the recipient of those reports can view them for a specified period of time, with the reports being secured such that the reports can not be saved or retained by the external server 905 in any manner. However, the server 903 is operable to transmit reports of linked information in any format desired and, as such, linked information may be electronically retained, printed onto paper or other suitable materials, and/or modified by the recipient, if desired.

It is also an object of the present invention to allow an entity outside of the production facility 901 to submit to the server 903, via the external server 905, certain information, preferences and/or business rules as to what linked information that entity may desire to see in one or more reports, which will be used by the server 903 to generate one or more reports for the entity, on an ongoing basis or otherwise. This may be accomplished on a one-time basis, thereby making it equivalent to a standing order for one or more reports containing the same linked information, or on numerous successive occasions, thereby allowing each ordered report to contain different linked information, and the production facility 901 may program the server 903 to receive such requests in any number of manners. For instance, the server 903 may be configured such that the external entity may create an account on the server whereby it will "log in" to the server 903 to submit a request for one or more reports, or the server 903 may be configured to allow requests to be received on a one-time basis, under certain circumstances, and each may be configured with one or more of a variety of standard payment options, as are known by those of skill in the art. For example, if the external entity is a drug company, that company may desire to receive and/or purchase reports containing linked information regarding the health and quality of certain organs 913 derived from livestock that had been administered a certain drug or combination of drugs produced by that drug company, in a variety of doses and/or amounts, or a certain drug or combination of drugs produced by a different drug company, such as a competitor, or they may elect to receive information regarding the health of organs 913 derived from livestock that are not presently purchasing drugs or combinations of drugs from the drug company. Under certain embodiments of the present invention, the drug company would be able to submit a request for one or more reports containing such linked information, to be generated on a one-time or ongoing, standing order-type basis, and it may submit this request directly to the production facility's 901 server 903. The production facility's 901 server 903 may be configured to require that the drug company provide certain information to the server 903 before the generated report(s) is transmitted, such as the drug company's name, address, contact person, means of payment, preferred format for the generated report(s), and similar information, in addition to the specifics regarding the linked information concerning organs, livestock, drugs or combination of drugs, and breeders to be included in such report(s). Should the drug company desire to create an account with the production facility's 901 server 903, this information may be retained by the server 903 to facilitate delivery of future generated reports. This way, the drug company may submit a request on a per-report basis, or it may create an account with instructions for the server 903 to generate and deliver reports of linked information on a continuing basis, such that the drug company may receive the same type of report for successive periods of time, such as annual, quarterly, monthly, weekly and/or daily reports containing certain linked information. The server 903 is thus operable in such a way so as to be able to receive such requests and/or to create and maintain such accounts, and to produce such reports, from a plurality of external servers 905. The server 903 is also operable to retain an accounting of all reports generated and delivered to external servers 905 so that accurate billing for the generated reports may be accomplished by the production facility 901.

Figure 10:
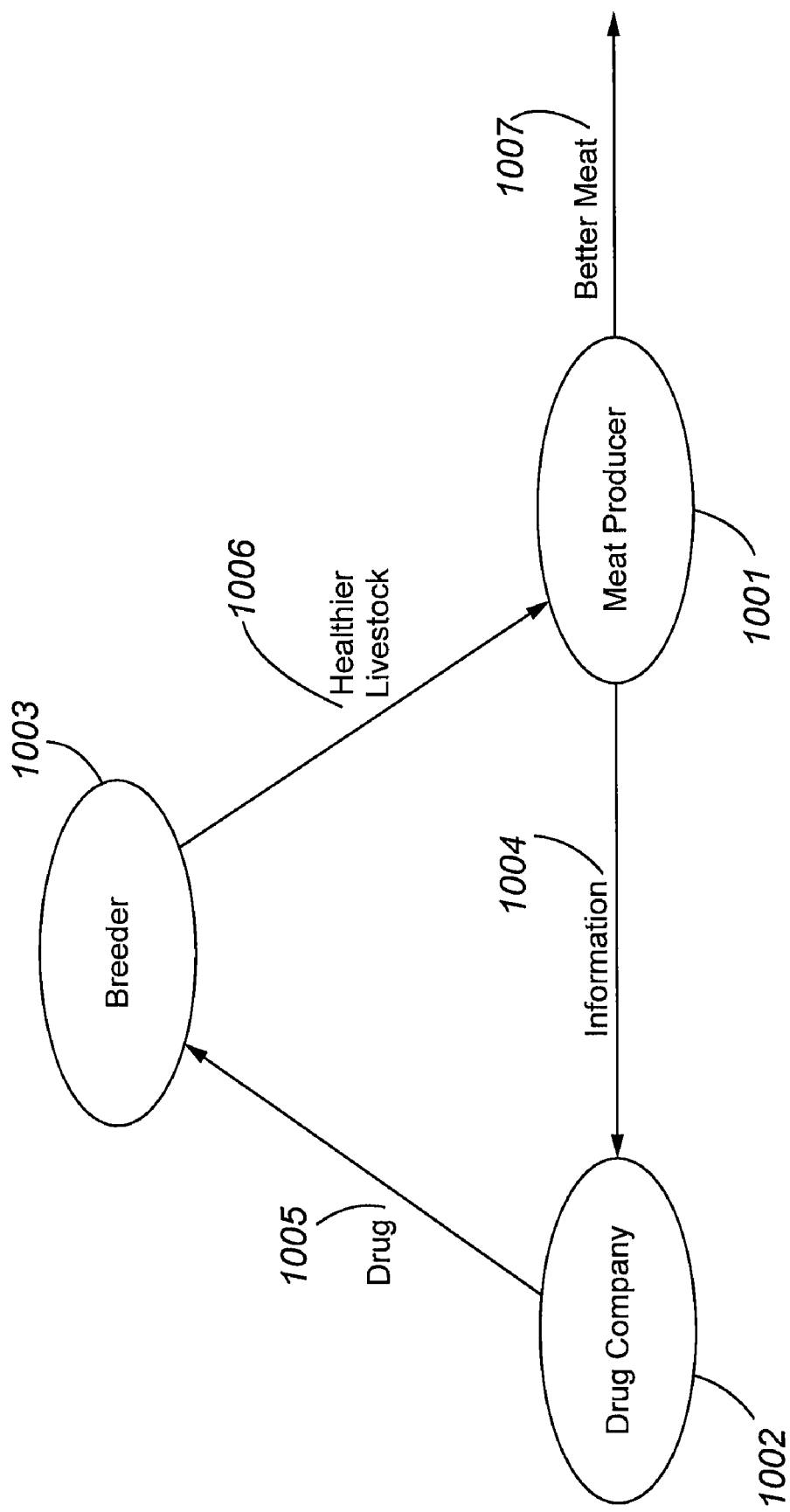
FIG. 10 is a block diagram depicting one method of administering a drug program related to livestock in accordance with at least some embodiments of the present invention.

Referring to FIG. 10, a method of administering a drug program related to livestock utilizing certain embodiments of the present invention is presented. As depicted therein, a meat producer 1001 is ultimately able to produce better meat 1007 because of the interrelationships made possible by the present invention. By utilizing certain embodiments of the system 900 described herein, the meat producer 1001 is able to generate one or more images that evidence the quality and/or grade actually given to animals, portions of animals, or organs derived from animals, that are delivered to it for slaughter by a breeder 1003, and is able to link that evidence to any number of data points and information that is input into, already existing and/or archived in the database 902 to generate one or more reports analyzing and summarizing this information. Such image evidence may thus be linked to information 1004 that may be of economic importance to a drug company 1002, such as whether or not a breeder 1003 has administered a drug or combination of drugs 1005 designed to increase the overall health of the breeder's 1003 animals, to its animals in advance of slaughter, and whether the drug company's drugs, as administered, are efficacious. The drug company 1002 will be able to order reports from the meat producer 1001 containing information regarding the use and efficacy of its drugs that produce effects capable of being captured by the image gathering means 904 of the system 900 of the present invention.

By way of example, presume that the drug company 1002 produces a drug 1005 containing the antibiotic tylosin (also known as tilmicosin), that is marketed as a pharmaceutical designed to increase the overall health of an animal, such as a cow, that is being prepared for slaughter by a fast conversion to a high protein diet. This drug 1005, being an antibiotic, would serve to reduce the cow's susceptibility to liver abscesses that commonly result from such a change in diet, thereby decreasing the total number of abscesses present in the cow's liver and increasing the health, quality and, ultimately, the grade given to the liver during the production process. Alternatively, the drug 1005 containing the antibiotic tylosin may be marketed as a pharmaceutical designed to reduce the incidence of respiratory disease in swine, which would serve to reduce the incidence and amount of lung tissue that attaches to the pleural membranes of a pig's rib cage in pigs suffering from certain respiratory diseases, thereby increasing the health and grade of the pig carcass being processed, as swine displaying little to no lung tissue attached to the pleural membranes lining the rib cage receive the highest quality rating and grades. Similarly, the drug 1005 containing the antibiotic tylosin may be marketed as a pharmaceutical designed to reduce the incidence of respiratory disease in cattle, which would serve a similar purpose as the pharmaceutical marketed for swine and ultimately serve to increase the health and grade of the cattle being processed. These effects, the presence or absence of liver abscesses and the presence or absence of lung tissue on the pleural membranes, are readily visible and can be viewed in an image captured by the image gathering means 904 of the present invention. Therefore, the visual effect of tylosin, or the absence of tylosin, on an organ, as captured in an image by the image gathering means 904 of the present invention, can be used as a means of determining whether tylosin was administered to the animal that organ was derived from in advance of slaughter. For instance, images generated by the image gathering means 904 of the present invention showing a large amount of lung tissue attached to the pleural lining of the rib case of a pig or cow and a high number of abnormalities (i.e. abscesses) on a beef liver can be used as visual evidence that a drug containing tylosin was not administered to an animal in advance of slaughter. In contrast, images showing little to no attached lung tissue and a negligible number of abnormalities can be used as visual evidence that such a drug was administered.

In addition to the foregoing, the visual effect of a drug captured by the image gathering means 904 of the present invention may also come from other portions of an animal, such as its muscle meat. For instance, a USDA quality grading of bovine meat is typically given based on several factors that affect the palatability (tenderness, juiciness, and flavor) of meat. These factors include, without limitation, the age of the animal, the firmness and texture of the meat derived from that animal, and the amount and distribution of marbling, or intramuscular fat, within the lean portion of the meat from that animal. Typically, beef carcass quality grading is based on the degree of marbling, which is the distribution of fat within the fibers of the lean muscle meat of an animal. To determine the overall quality and grading of an animal, USDA graders typically evaluate the amount and distribution of marbling in the rib eye muscle, between the 12th and 13th ribs, by visually inspecting the meat along the production line. The result of the inspection is called a "Preliminary Yield Grade" and the determined quality of the rib eye, by USDA standards, is deemed indicative of the quality and grade of the entire animal. As may be appreciated, the degree of marbling of a rib eye can also be captured visually by the image gathering means 904 of the present invention, such that the image, showing the degree of marbling, together with image evidence captured by the image gathering means 904 of the USDA inspection stamps, as described above, can be sent to the server 903, where it can be linked to other information regarding the animal the rib eye was derived from, such as the administration of a drug or drug program to that animal in advance of slaughter.

For example, presume that the drug company 1002 produces a drug 1005 containing either racoptamine hydrochloride or zilpaterol hydrochloride, both of which are beta receptor agonists similar in structure and pharmacology to catecholamine derivatives. This drug 1005 may be marketed as a pharmaceutical designed to increase lipolysis and reduce lipogenesis in cattle, which would serve to increase a cow's live weight gain and red meat yield, thereby increasing the quality and, ultimately, the grade given to the cow, all without impacting the marbling of the rib eye. As can be appreciated, this will serve to yield higher quality meat products that sell at a higher price, increasing the profits available for the meat producer 1001 and the breeder 1003. Alternatively, the drug 1005 containing racoptamine hydrochloride may be marketed as a pharmaceutical designed to increase lipolysis and reduce lipogenesis in swine, which would serve to increase a pig's live weight gain and lean meat yield, thereby increasing the quality and, ultimately, the grade given to the pig, thereby yielding higher quality meat products that sell at a higher price. The effects of these beta receptor agonists are readily visible and can be viewed in an image captured by the image gathering means 904 of the present invention. Therefore, the visual effect of racoptamine hydrochloride or zilpaterol hydrochloride, or the absence of racoptamine hydrochloride or zilpaterol hydrochloride, on the rib eye or other meat used for quality grading purposes, as captured in an image by the image gathering means 904 of the present invention, can be used as a means of determining whether racoptamine hydrochloride or zilpaterol hydrochloride was administered to an animal in advance of slaughter. For instance, images generated by the image gathering means 904 of the present invention showing a large amount of lean muscle mass and a high degree of marbling in the rib eye or similar meat can be used as visual evidence that a drug containing racoptamine hydrochloride or zilpaterol hydrochloride was administered to an animal in advance of slaughter. In contrast, images showing little lean muscle mass and a negligible degree of marbling of the rib eye or similar meat can be used as visual evidence that such a drug was not administered.

These types of beta receptor agonists are used more frequently in certain breeds of cattle, such as male Holsteins and other exotic breeds of cattle, which are not usually bred and raised for meat production. Holsteins, being a breed typically used by the dairy industry, tend to be raised and kept by certain specialized farms and ranches and are not typically bred by commercial meat breeders 1003. It thus may be useful to identify the breed of cattle being visually inspected by the image gathering means 904 before obtaining the image of the rib eye to determine whether a drug or combination of drugs was administered to the cow in advance of slaughter, as certain breeds such as Holsteins are likely to have always been administered this drug and capturing an image in its rib eye may not provide any additional useful information. However, the presence of a Holstein in a lot of cattle can help pinpoint a feed lot of origin much more effectively than other breeds, as the number of potential feedlots of origin it could have come from is limited to dairy lots, which are more limited in number and geography than meat production feedlots. Therefore, the identification of a Holstein breed in a particular lot of origin is still useful information that can be linked to other information of interest to the drug company 1002.

The drug 1005 of interest to the drug company 1002 need not be limited to a single drug but may be a combination of drugs, each designed to increase the overall health of livestock to be delivered to the meat producer 1001 for slaughter. For example, the drug 1005 may consist of at least two drugs, one that does not necessarily have an effect on the health of the animal that is readily captured by an image obtained by the systems of the present invention, and a second that does produce an effect capable of being captured by such an image and that serves to readily distinguish the presence of the second drug from the absence of the second drug. The second drug, in addition to serving to increase the overall health of the animal it is administered to, may thus serve as an indicator as to whether the combination of drugs 1005 is being administered. In this instance, the drug company 1002 could obtain reports of linked information 1004 from the meat producer 1001 concerning the effect of the second drug on a breeder's 1003 animals, which would serve to indicate whether that breeder 1003 is administering the combination of drugs 1005 to its livestock. By way of example, presume that the first drug is a drug such as monensin sodium, which is designed to prevent and control the growth of certain coccidial bacteria (such as *E. zuernii* and *E. bovis*), and thus prevent coccidiosis. While this drug will certainly serve to increase the overall health of an animal, it is likely that it would not have an effect that is readily captured by an image generated by the present invention. It may therefore be administered concurrently with a second drug such as tylosin. As described above, the effect of tylosin is quite apparent in that a treated animal will display readily visible effects, such as a decrease in the number and severity of liver abscesses versus an untreated liver or a reduction in the amount of lung tissue attached to the pleural membranes, an image of which can be readily captured by the image gathering means 904 of the present invention. Therefore, when administered in combination, the effect of tylosin, the second drug and in this case the indicator drug, can be used as a means of determining, visually, whether tylosin was administered to an animal in advance of slaughter. Since monensin sodium, the first drug, is administered together with tylosin, the effect of tylosin can also be used as a means of determining, visually, whether monensin sodium was administered to an animal in advance of slaughter.

By and through embodiments of the present invention, the drug company 1002 may utilize the server 903 to order reports from the meat producer 1001 containing visual information regarding the effect of its drugs, such as those described above among others, that produce effects capable of being captured by the image gathering means 904 of the system 900 of the present invention. The drug company 1002 may utilize this information in many ways, such as evaluating whether a particular drug or combination of drugs 1005 is effectively treating a particular malady or improving the health of livestock in the manner intended, whether certain breeders 1003 are using the drug company's 1002 products so as to more effectively focus its marketing efforts, and others. The drug company 1002 may elect to contact the meat producer 1001 to request information 1004 on one or more breeders 1003 that the drug company believes may not be purchasing and/or administering one or more of the drug company's 1002 drugs 1005 to their livestock in advance of slaughter. Specifically, the drug company 1002 may request that the meat producer 1001 provide the drug company with information 1004 consisting of image data showing the quality and grade given to the organs and/or rib eyes derived from a breeder's 1003 animals, linked to the contact information for that breeder 1003 and to information provided to the meat producer 1001 by the breeder 1003 as to whether or not a drug was administered to such livestock. Upon receipt of this request, the meat producer 1001 is able to utilize the system 900 of the present invention to generate a report containing this information 1004, and is able to transmit this information 1004 to the drug company 1002 via the means described herein. The drug company 1002 can then visualize the linked information 1004 contained in the report and determine whether the breeder 1003 is, in fact, purchasing and administering the drug 1005. In the event that the breeder 1003 is not utilizing the drug 1005, the drug company 1002 may use the report of linked information 1004 to market the drug 1005 to the breeder 1003. Alternatively, as a means of bolstering its marketing efforts, the drug company 1002 may request that the meat producer 1001 send it information 1004 regarding the quality and grading of animals that have been administered one or more of the drug company's 1002 drugs 1005, in order to demonstrate to one or more breeders 1003 that the drugs 1005 do serve to increase the health and quality of animals. Based on this marketing effort, the breeder 1003 may elect to purchase the drug 1005 and administer it to its animals, which will cause the breeder 1003 to produce healthier livestock 1006 for delivery to the meat producer 1001. As will be appreciated, the receipt of healthier livestock 1006 allows the meat producer 1001 to produce and sell better meat 1007. In the event that the breeder 1003 is administering the drug 1005 to its livestock 1006, the drug company may utilize the information 1004 obtained from the meat producer 1001 to determine whether to continue the sale of the drug 1005 to the breeder 1003 on existing terms, or whether to adjust the price of the drug 1005, according to the information 1004 obtained. For example, the drug company 1002 may have elected to sell the drug 1005 to the breeder 1003 initially at a reduced rate, in order to gain business and sell its product. If, based on the information 1004 obtained from the meat producer 1001, it is evident that the drug 1005 is serving to allow the breeder 1003 to produce healthier livestock 1006, then the drug company may elect to increase the sale price of the drug 1005 to the breeder 1003, based on an actual increase in livestock health, as shown by the information 1004 contained on reports generated by the meat producer 1001.

Figure 11:
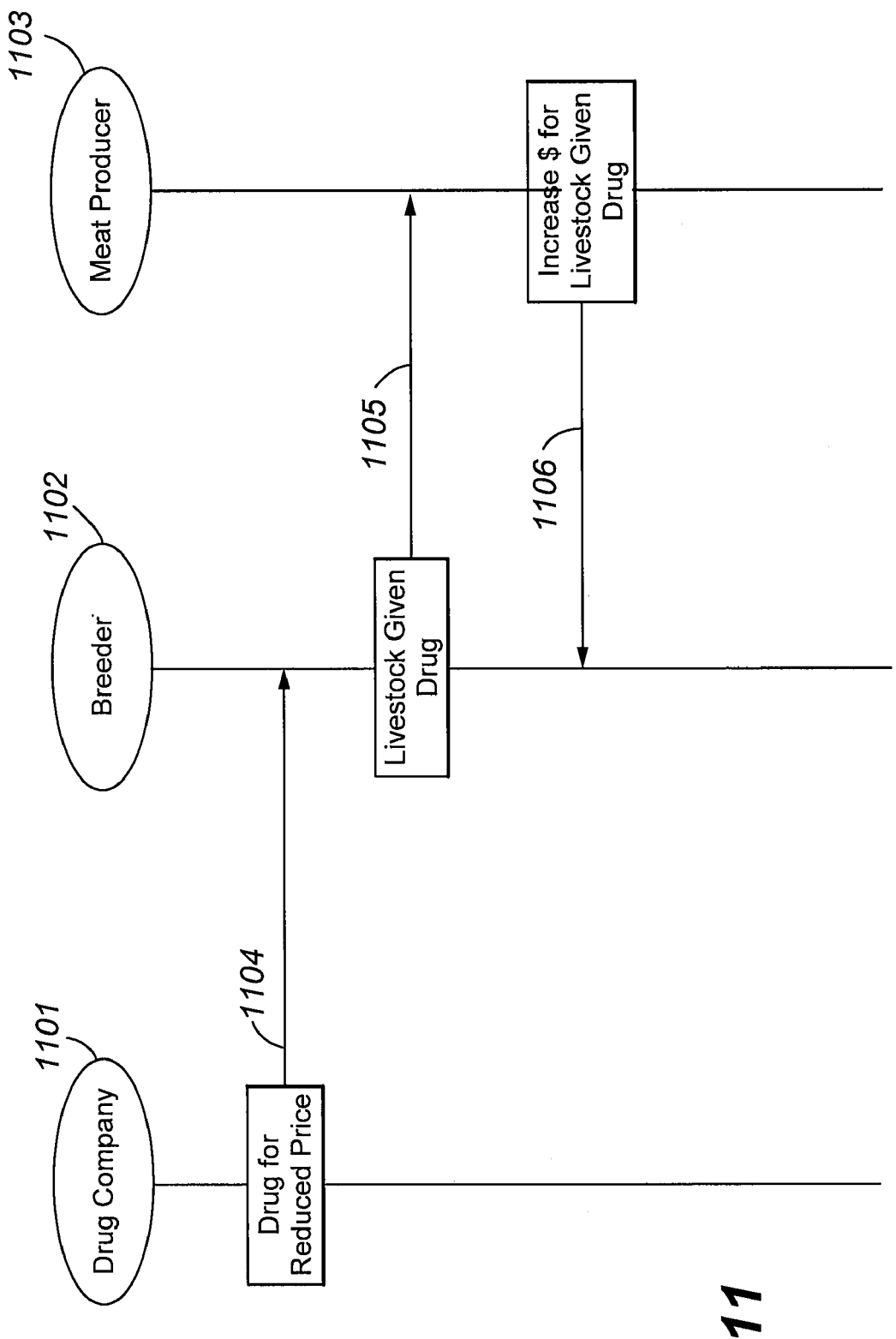
FIG. 11 shows another method for administering a drug program related to livestock in accordance with at least some embodiments of the present invention.

Referring to FIG. 11, another embodiment of a method for administering a drug program related to livestock utilizing certain embodiments of the present invention is presented. In this embodiment, the drug company 1101 is marketing and selling a drug to a livestock breeder 1102 for a reduced price (step 1104). The drug company 1101 may be doing this for any number of reasons, including, without limitation, utilizing a reduced price in an attempt to introduce a new drug to the market, or as an introductory rate in an attempt to induce the breeder 1102 to purchase the drug on an ongoing basis. As before, the drug in question need not be a single drug, but may be a combination of one or more drugs. The breeder 1102 purchases the drug for a reduced price (step 1104) and administers it to all, or a portion, of his or her livestock (step 1105) prior to delivering the livestock to the meat producer 1103 for slaughter. The breeder 1102 benefits from the reduced price by paying less money for it, but also in that he or she need not continue to purchase the drug if it does not serve to increase the quality and health of the breeder's 1102 livestock. Preferably, the breeder 1102 administers the drug to only a specific, identifiable portion of his or her livestock (step 1105), so as to provide a basis for comparing the quality and health of the animals that receive the drug with those that do not.

After administering the drug to his or her livestock (step 1105), the breeder 1102 delivers the livestock to the meat producer 1103 for slaughter. The meat producer 1103 will typically pay the breeder 1102 a set amount for the livestock upon delivery, on a per pound basis. In the present embodiment, the meat producer 1103 pays the breeder 1102 a typical per-pound rate for the livestock, with the understanding that the meat producer 1103 will pay the breeder 1102 a bonus for those animals that yield carcasses or meat products, and preferably organs and/or rib eyes, that receive a certain minimum USDA grade and/or quality rating.

The meat producer 1103 will be able to utilize the system 900 described herein to track the livestock delivered by the breeder 1102 through the production process. By using the system 900, the meat producer 1103 will be able to generate one or more reports that link image data showing the quality rating and/or grade given to a carcass, meat product or organ to the specific lot of animals delivered by the breeder 1102 and, more importantly, to a specific animal. The meat producer 1103 will thus be able to determine which animals delivered meet the minimum quality and grading standards agreed upon, and can pay the breeder 1102 an increased amount of money for only those animals that meet these requirements (step 1106). By utilizing the reports of linked information in this manner, the meat producer 1103 is providing a financial incentive to the breeder 1102 to provide healthier, higher quality livestock for slaughter. Alternatively, the meat producer 1103 can require that a certain percentage of the breeder's 1102 livestock meet the minimum acceptable requirements before any increase in money will be paid. This way, the meat producer 1103 need not pay additional money for small percentages of better quality animals, which may be attributable to random chance rather than the administration of a drug or combination of drugs to the breeder's 1102 livestock in advance of slaughter.

Additionally, the breeder 1102 may acquire the same reports utilized by the meat producer 1103 so as to be able to determine whether the animals given the drug (step 1105) were those that reached the minimum standards of quality and grading and were thus of greater profit to the breeder 1102. This way, the breeder 1102 will be able to determine whether the specific, identifiable animals that were given the drug company's 1101 drug(s) in advance of slaughter were those identified on the meat producer's 1103 reports as being of higher quality and receiving a higher grade. Based on this information, the breeder 1102 can determine whether to continue to purchase the drug(s) from the drug company 1101 and administer it/them to his or her livestock. In the event that the drug served to increase the overall quality and health of the livestock, both the drug company 1101 and the meat producer 1103 will have induced the breeder 1102 into administering a drug program to his or her livestock by providing financial incentives for the breeder 1102 to purchase and administer the drug in question.

Figure 12:
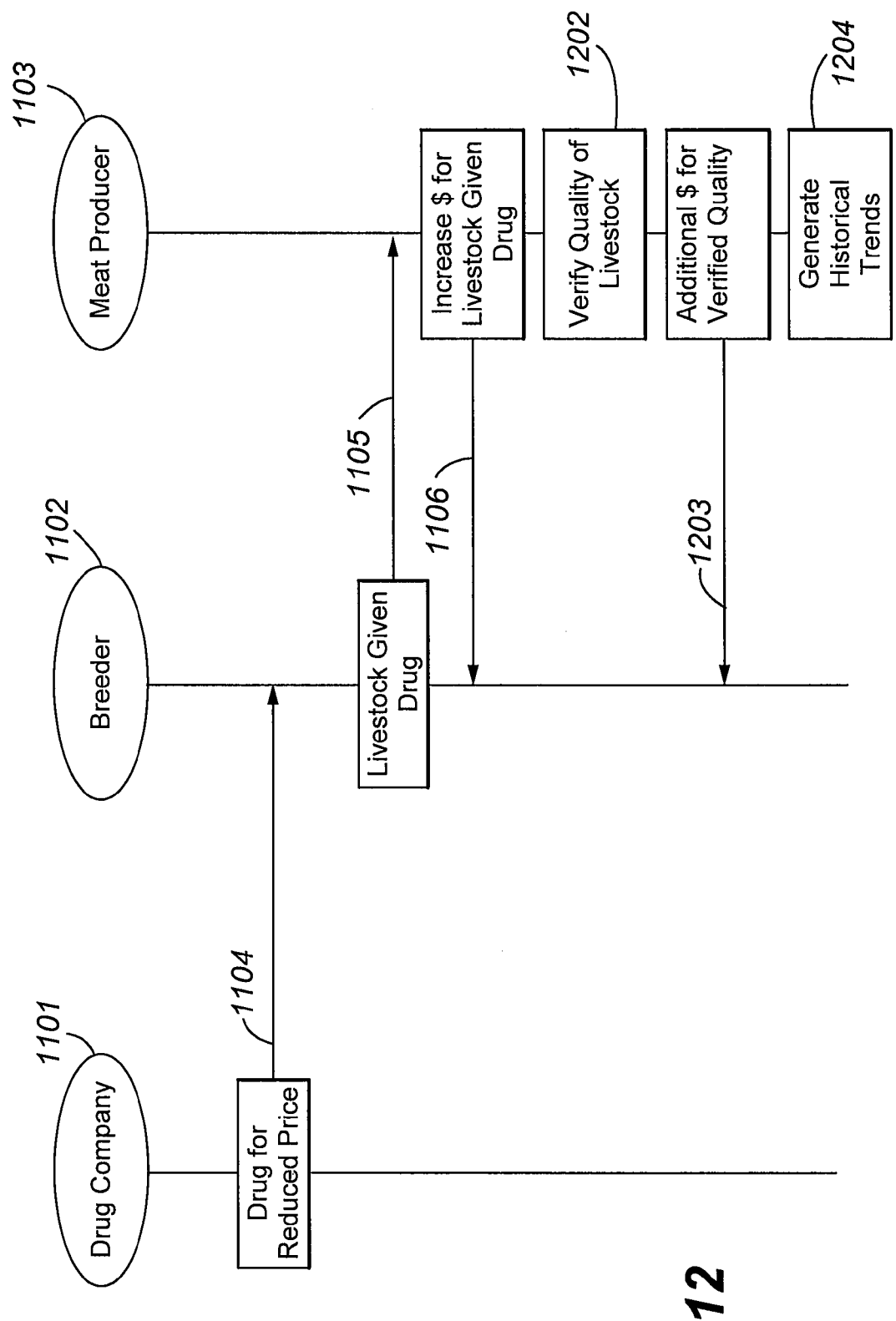
FIG. 12 shows an alternate embodiment to the method for administering a drug program related to livestock in accordance with at least some embodiments of the present invention presented in FIG. 11.

Referring now to FIG. 12, an alternate embodiment of the method for administering a drug program related to livestock presented in FIG. 11 will be described. As with the previous embodiment, in this embodiment the drug company 1101 is marketing and selling a drug to a livestock breeder 1102 for a reduced price (step 1104), and the drug in question need not be a single drug, but may be a combination of one or more drugs. The breeder 1102 purchases the drug for a reduced price (step 1104) and administers it to all, or a portion, of his or her livestock (step 1105) prior to delivering the livestock to the meat producer 1103 for slaughter. The breeder 1102 benefits from the reduced price in that he or she is not paying full price at the outset and need not continue to purchase the drug if it does not serve to increase the quality and health of the breeder's 1102 livestock. In this embodiment, it is preferable that the breeder 1102 administer the drug to all of his or her livestock (step 1105) and indicate to the meat producer 1103, upon delivery of the livestock for slaughter, that the drug has been administered (step 1105) in an effort to increase the quality and health of the livestock. It is also preferable that the breeder 1102 indicate to the meat producer 1103 what drug has, or what combination of drugs have, been administered, and that the meat producer 1103 ensure that this information is collected from the breeder 1102 upon delivery of the livestock.

In this embodiment, the meat producer 1103 pays the breeder 1102 a typical amount of money for the livestock delivered (step 1201), notwithstanding the assertion that the drug has been administered to all of the livestock in question, with the understanding that the meat producer 1103 will pay the breeder 1102 a bonus for those animals that yield carcasses or meat products, and preferably organs, that receive a certain minimum USDA grade and/or quality rating. In the event that the breeder 1102 elects to administer the drug (step 1104) to only a portion of his or her animals, the meat producer 1103 may determine to pay the bonus to the breeder 1102 for those animals that meet the minimum quality and grading standards and that have been given the drug(s).

The meat producer 1103 will be able to utilize the system 900 described herein to track the livestock delivered by the breeder 1102 through the production process, as well as gather and link together information relevant to the quality and health of such livestock. By using the system 900, the meat producer 1103 will be able to generate one or more reports that link image data showing the quality rating and/or grade given to a carcass or meat product, and preferably an organ or rib eye, to the specific lot of animals delivered by the breeder 1102 and, more importantly, to a specific animal. The meat producer 1103 will also be able to include with these reports the linked information as to which animals were given the drug prior to delivery for slaughter, thereby verifying the quality and health of the livestock purported to have received the drug (step 1202). The meat producer 1103 can then pay the breeder 1102 the bonus for only those animals that actually meet the minimum standards of quality and grading and, if the agreement regarding the bonus requires the presence of the drug in question, that have been administered the drug (step 1203). By utilizing the reports of linked information in this manner, the meat producer 1103 is providing a financial incentive to the breeder 1102 to administer a drug program to his or her livestock prior to slaughter that is based on not only the presence of the drug in the animals, but also certain minimum standards of quality and grading. In addition to the foregoing, the meat producer 1103 can utilize the system 900 described herein to store the reports generated on the breeder's 1102 livestock, thereby allowing the meat producer 1103 to be able to generate reports containing historical trends on the quality and health of the livestock produced by that breeder 1102 over time (step 1204), as well as whether the drug in question serves to increase the health of such livestock produced by that breeder 1102.

Figure 13:
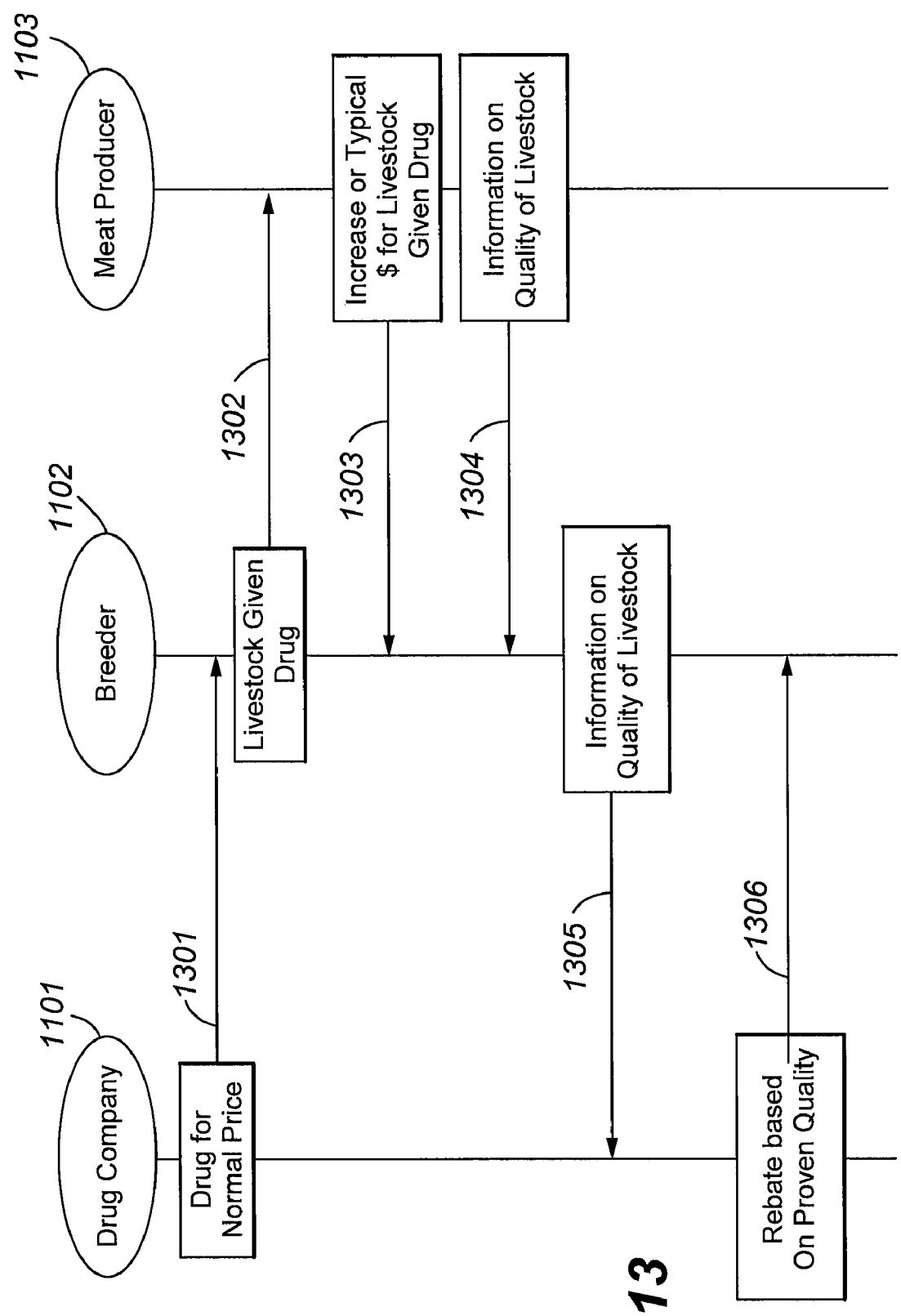
FIG. 13 shows a third method for administering a drug program related to livestock in accordance with at least some embodiments of the present invention.

Referring to FIG. 13, a third embodiment of a method for administering a drug program related to livestock utilizing certain embodiments of the present invention is presented. In this embodiment, the drug company 1101 is marketing and selling a drug or combination of drugs to a livestock breeder 1102 at a normal price (step 1301), with the understanding that the drug company 1101 will provide the breeder 1102 with a rebate at a future point in time, provided that the breeder 1102 can provide the drug company 1101 with evidence that the drug(s) in question was/were actually administered to the breeder's 1102 livestock. In this embodiment, the drug company 1101 has reason to believe that the drug(s) in question has/have been proven to increase the quality and health of livestock and is basing the rebate on this fact. Therefore, in the event that the breeder 1102 claims that a rebate is due, but cannot provide evidence of an actual increase in health and quality of the breeder's 1102 livestock, the drug company 1101 will know that the drugs were not administered to the livestock for which the rebate is claimed. As before, the drug in question need not be a single drug, but may be a combination of one or more drugs. The breeder 1102 purchases the drug at its normal rate (step 1301) and administers it to all, or a portion, of his or her livestock (step 1302) prior to delivering the livestock to the meat producer 1103 for slaughter. Preferably, the breeder 1102 administers the drug to all of his or her livestock (step 1302) and indicates to the meat producer 1103 that the drug has been administered (step 1302) in an effort to increase the quality and health of the livestock. It is also preferable that, upon delivery of the livestock, the breeder 1102 indicates to the meat producer 1103 what drug has, or what combination of drugs have, been administered.

After administering the drug to his or her livestock (step 1302), the breeder 1102 delivers the livestock to the meat producer 1103 for slaughter, who pays the breeder 1102 a typical per-pound rate for the livestock (step 1303). Alternatively, the meat producer 1103, at its option, may elect to pay the breeder 1102 an increase over the typical per-pound rate on the basis that the drug in question has been administered to the livestock (step 1303). The meat producer 1103 will be able to utilize the system 900 described herein to track the specific lot of livestock delivered by the breeder 1102 through the production process, as well as to collect and link together information relevant to the health and quality grading of the livestock delivered. By using the system 900, the meat producer 1103 will be able to generate one or more reports that link image data showing the quality rating and/or grade given to the carcasses or meat products, and preferably organs, derived from the specific lot of animals delivered by the breeder 1102, thereby providing image data showing the quality and/or grading each animal in the lot received. The meat producer 1103 will also be able to link to the reports information regarding the administration of the drug to the lot of animals in question in advance of slaughter, thereby providing a report showing the quality and/or grading given to each individual animal in the lot in question along with the presence of the drug in question.

The breeder 1102 may then obtain these reports from the meat producer 1103 (step 1304) in order to have the proof required by the drug company 1101 of the administration of the drug. The breeder 1102 then provides the reports to the drug company 1101 (step 1305), together with a request for the rebate, pursuant to the agreement between the drug company 1101 and the breeder 1102. The drug company 1101 will then provide the rebate promised (step 1306), based on the evidence contained in the reports generated by the meat producer 1103. By utilizing the reports of linked information generated by the meat producer 1103 in this manner, the breeder 1102 is able to receive a financial incentive to purchase and administer the drug in question in an effort to provide healthier, higher quality livestock for slaughter, and will be able to determine whether the administration of the drug (step 1302) actually served to increase the quality and health of his or her livestock. The drug company 1101 is also able to require that a breeder 1102 provide evidence of actual use of the drug before giving any rebate, or similar financial incentive, to the breeder 1102 for the purchase of the drug.

Figure 14:
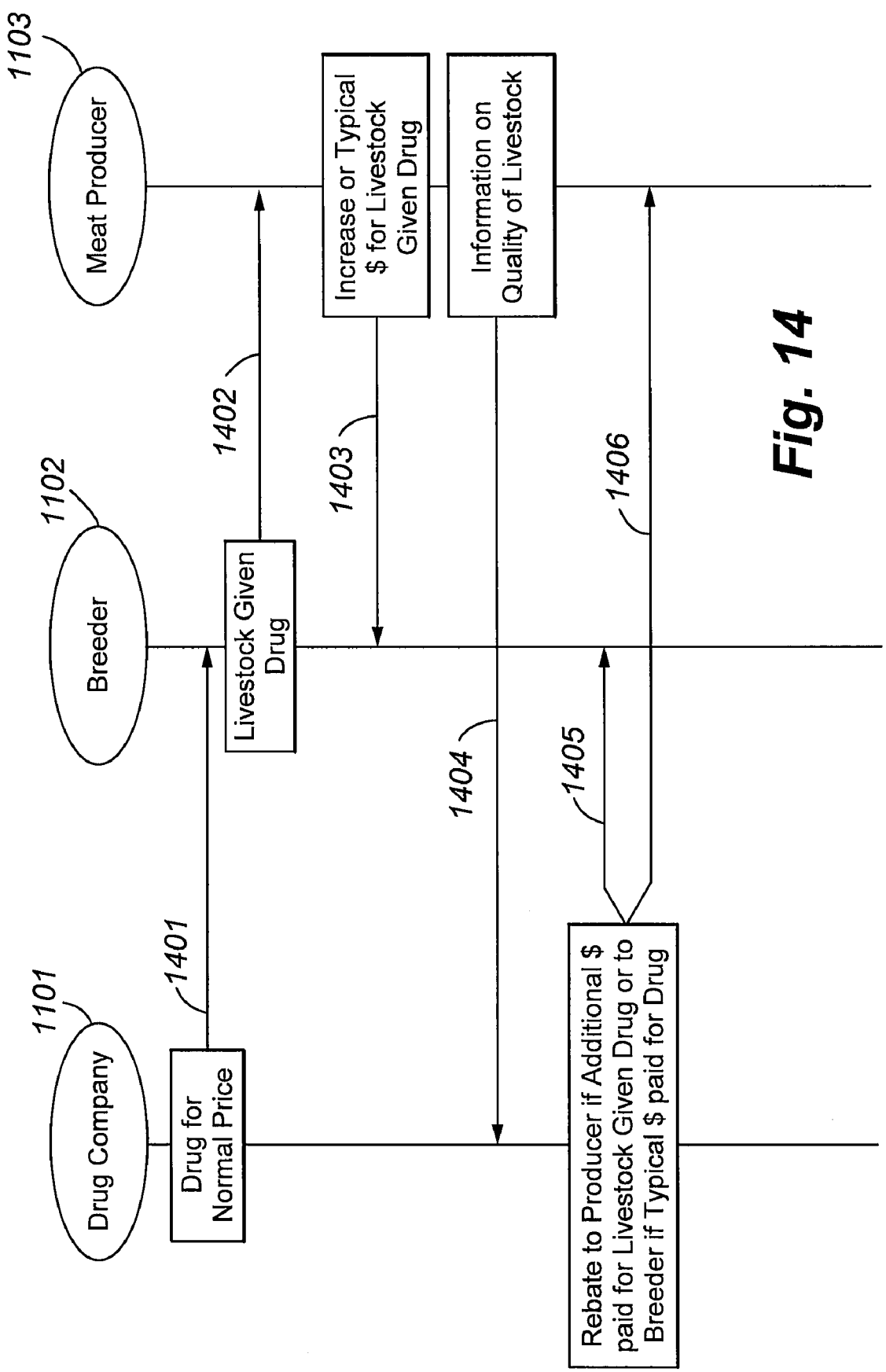
FIG. 14 shows a fourth method for administering a drug program related to livestock in accordance with at least some embodiments of the present invention.

Referring to FIG. 14, a fourth embodiment of a method for administering a drug program related to livestock utilizing certain embodiments of the present invention is presented. In this embodiment, the drug company 1101 is marketing and selling a drug to a livestock breeder 1102 at a normal price (step 1401), and may have reached the same agreement with the breeder 1102 described in the previous embodiment, as before. Alternatively, the drug company 1101 may have reached an agreement with the meat producer 1103 whereby the drug company 1101 agrees to reimburse the meat producer 1103 a certain amount of money if the meat producer 1103 agrees to pay those breeders 1102, that are known customers of the drug company 1101, a higher per-pound rate for livestock that have been administered the drug company's 1101 drugs, provided that the meat producer 1103 can provide the drug company 1101 with evidence that the drug in question was actually administered to the livestock that received the higher per-pound rate by the meat producer 1103. Either of these two agreements is contemplated for use with the present embodiment. As with the previous embodiment, the drug company 1101 has reason to believe that the drug in question has been proven to increase the quality and health of livestock and is basing the money to be paid, in either arrangement, on this fact. As before, the drug in question need not be a single drug, but may be a combination of one or more drugs.

The breeder 1102 purchases the drug at its normal rate (step 1401) and administers it to all, or a portion, of his or her livestock (step 1402) prior to delivering the livestock to the meat producer for slaughter. Preferably, the breeder 1102 administers the drug to all of his or her livestock (step 1402) and indicates to the meat producer 1103, upon delivery, that the drug company's 1101 drug(s) has/have been so administered in an effort to increase the quality and health of the breeder's 1102 livestock. Depending upon the parties to the agreement reached in this embodiment, the meat producer 1103 will either pay the breeder 1102 a normal per-pound rate, or an increase over the normal per-pound rate, for the livestock delivered (step 1403). In the event that the agreement reached is between the drug company 1101 and the breeder 1102, the meat producer 1103 will pay the breeder 1102 a normal per-pound rate (step 1403), as the breeder 1102 will be able to recover some of its costs from the drug company 1101 through a rebate on the price of the drug (step 1405). In the event that the agreement reached is between the drug company 1101 and the meat producer 1103, the meat producer 1103 will pay the breeder 1102 an increase over the per-pound rate (step 1403), as the meat producer 1103 will be able to recover some of its costs from the drug company 1101 through a rebate equal to, at least, the total amount of the increase paid to the breeder 1102 (step 1406).

After administering the drug to his or her livestock (step 1402), the breeder 1102 delivers the livestock to the meat producer 1103 for slaughter, who pays the breeder 1102 a per-pound rate for the livestock that is in accordance with the nature of the agreement, as described above (step 1403). The meat producer 1103 will be able to utilize the system 900 described herein to track the specific lot of livestock delivered by the breeder 1102 through the production process and to gather and link together information relative to the health and quality rating of the delivered livestock. By using the system 900, the meat producer 1103 will be able to generate one or more reports that link pictorial evidence of the quality rating and/or grade given to the carcasses or meat products, and preferably organs, derived from the specific lot of animals delivered by the breeder 1102, thereby providing image data showing the quality and/or grading each animal in the lot received. The meat producer 1103 will also be able to link to the reports information regarding the administration of the drug company's 1101 drug to the lot of animals in question in advance of slaughter, thereby providing a report showing the quality and/or grading given to each individual animal in the lot in question along with the presence of the drug in question.

The drug company 1101 may then obtain these reports from the meat producer 1103 (step 1404) in order to have proof of the administration of the drug to the specific lot of livestock, as well as proof of the amount paid to the breeder 1102 by the meat producer 1103 for such livestock. The drug company 1101 utilizes the information presented in the reports generated by the meat producer 1103 to verify that their drug has been administered to the lot of livestock in question, and then provides a rebate to either the breeder 1102 or the meat producer 1103, pursuant to the specific agreement reached. If the agreement is between the drug company 1101 and the breeder 1102, then the drug company 1101 provides the breeder 1102 with a rebate on the price of the drug (step 1405), as described in the previous embodiment. If the agreement is between the drug company 1101 and the meat producer 1103, then the drug company 1101 will refund at least the increase over the typical per-pound rate paid by the meat producer 1103 (step 1406), based on the evidence contained in the reports generated by the meat producer 1103 that the drug company's 1101 drug was actually used by the breeder 1102.

Figure 15:
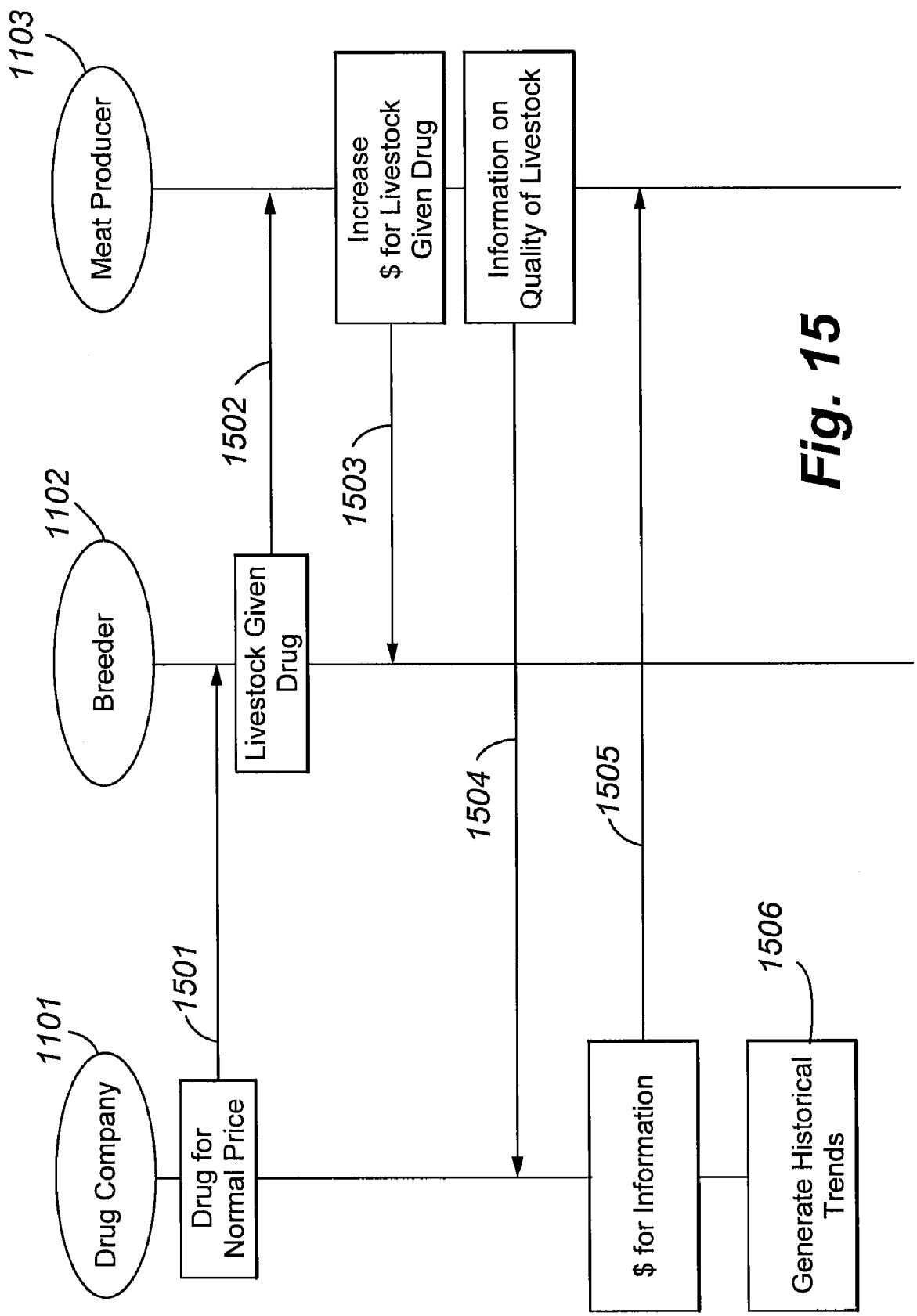
FIG. 15 shows a fifth method for administering a drug program related to livestock in accordance with at least some embodiments of the present invention.

Referring to FIG. 15, a fifth embodiment of a method for administering a drug program related to livestock utilizing certain embodiments of the present invention is presented. In this embodiment, the drug company 1101 is marketing and selling a drug to a livestock breeder 1102 at a reduced price (step 1501), with the understanding that the meat producer 1103 will pay the breeder 1102 an increase over the typical per-pound rate upon delivery of the breeder's 1102 livestock for slaughter. In this embodiment, the drug company 1101 is interested in purchasing information as to the efficacy of the drug in question and/or the use of the drug by one or more breeders 1102 and is willing to provide a financial incentive to the meat producer 1103 to obtain such information, as the drug company 1101 will then purchase reports generated by the system 900 of the present invention from the meat producer 1103 concerning the breeder's 1102 livestock and the efficacy of the drug(s) in such livestock. As before, the drug in question need not be a single drug, but may be a combination of one or more drugs.

The breeder 1102 purchases the drug at a reduced rate (step 1501) and administers it to all, or a portion, of his or her livestock (step 1502) prior to delivering the livestock to the meat producer for slaughter. Preferably, the breeder 1102 administers the drug to all of his or her livestock (step 1502). It is also preferable that the meat producer 1103 inquire as to whether the drug has been given to the breeder's 1102 livestock when such livestock are delivered for slaughter, and may require the breeder 1102 to provide this information as a prerequisite to payment of the amount over the typical per pound rate. Provided that the breeder 1102 informs the meat producer 1103 that the drug(s) has/have been administered, the meat producer 1103 pays the breeder 1102 an increase over the typical per-pound rate for the livestock (step 1503), but only for those animals the breeder 1102 indicates have been given the drug company's 1101 drug. The meat producer 1103 will be able to utilize the system 900 described herein to track the specific lot of livestock delivered by the breeder 1102 through the production process and to gather and link together information relative to the health and quality grading of the livestock. By using the system 900, the meat producer 1103 will be able to generate one or more reports that link image data showing the quality rating and/or grade given to the carcasses or meat products, and preferably organs and rib eyes, derived from the specific lot of animals delivered by the breeder 1102, thereby providing pictorial evidence of the quality and/or grading each animal in the lot received. The meat producer 1103 will also be able to link to the reports information regarding the administration of the drug company's 1101 drug to the lot of animals in question in advance of slaughter, thereby providing a report showing the quality and/or grading given to each individual animal in the lot in question along with the presence of the drug in question.

The drug company 1101 then obtains the reports generated by the meat producer 1103 (step 1504) in order to verify the administration of the drug to the lot of livestock in question. The drug company 1101 will then rebate the amount paid above the typical per-pound rate to the meat producer 1103 (step 1505), based on the evidence contained in the reports generated by the meat producer 1103. Additionally, the drug company 1101 may pay the meat producer 1103 for the linked information presented in the reports generated by the meat producer 1103 (step 1505), as such information may be used to generate historical trends as to which breeders 1102 are purchasing and administering the drug company's 1101 drugs and/or whether that drugs serve to actually increase the overall health and quality of livestock (step 1506), which the drug company 1101 may use in future marketing, research and development efforts.

The present invention, in various embodiments, includes components, methods, processes, systems and/or apparatus substantially as depicted and described herein, including various embodiments, sub combinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included descriptions of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for administering a drug program related to an animal, comprising:
    receiving a digital image of an organ from an animal depicting the quality or grading of said organ;
    determining an animal from which the organ was derived;
    associating the digital image and the determined animal with the presence or absence of a drug or combination of drugs that was previously administered to an animal; and
    using a processor, evaluating, by reference to the digital image depicting the organ, whether the determined animal has been treated with the drug or combination of drugs, wherein said evaluating step comprises determining the presence of abnormalities of said organ.

2. The method of claim 1, wherein the organ is selected from the group consisting of brain, liver, tongue, pancreas gland, thymus gland, stomach, feet, kidney, lungs, heart, small intestine, testicles, placenta, crop and caul.

3. The method of claim 1, wherein the digital image is viewable in real time as said organ is passed within a field of view of a means for generating an image.

4. The method of claim 1, wherein said step of determining comprises correlating an identifying number of an individual animal with said organ.

5. The method of claim 1, wherein the drug is an antibiotic drug.

6. The method of claim 5, wherein the antibiotic drug is tylosin.

7. The method of claim 1, wherein the animal is a bovine, porcine or ovine animal.

8. The method of claim 1, wherein the drug is a beta receptor agonist drug.

9. The method of claim 8, wherein the beta receptor agonist drug is selected from the group consisting of racoptamine hydrochloride and zilpaterol hydrochloride.

10. The method of claim 1, further comprising generating a report containing information regarding the presence or absence of a drug, combination of drugs, or drug program in the determined animal.

11. The method of claim 3, wherein said means for generating an image is selected from the group consisting of a digital color camera, a digital black and white camera, and a digital video camera.

12. The method of claim 1, wherein the combination of drugs elicits an effect that is viewable in said digital image.

13. A method for administering a drug program related to an animal, comprising:
    separating at least one organ of interest from other organs;
    grading the at least one organ of interest; capturing an image of the at least one organ of interest;
    associating the at least one organ of interest and the image with at least one of: a) an animal and b) a lot of origin;
    analyzing the image to determine the grade of the at least one organ of interest;
    associating the determined grade of the at least one organ of interest with the at least one of an animal and lot of origin; and
    using a processor, determining the presence or absence of an administered drug or combination of drugs for one of the at least one of an animal and lot of origin, wherein said determining step comprises accessing the presence of abnormalities of said at least one organ.

14. The method of claim 13, wherein the at least one organ of interest is selected from the group consisting of brain, liver, tongue, pancreas gland, thymus gland, stomach, feet, kidney, lungs, heart, small intestine, testicles, placenta, crop and caul.

15. The method of claim 13, wherein the animal is a bovine, porcine or ovine animal.

16. The method of claim 13, wherein the image is a digital image and is viewable in real time as said organ is passed within a field of view of at least one of a digital color camera, a digital black and white camera, or a digital video camera.

17. A method for determining whether an animal was administered a drug, comprising:
    capturing an image of a liver of an animal after the animal has been slaughtered by having said liver scanned within a field of view of a means for generating an image;
    associating the image with a lot of origin of the animal;
    using a processor, analyzing the image to determine whether the liver indicates that the animal has experienced infection or disease, said analyzing step comprising a review of visual evidence of liver abnormalities;
    and determining whether the animal was previously administered a drug or combination of drugs.

18. The method of claim 17, wherein the step of capturing comprises generating a digital image and said means for generating an image is selected from the group consisting of a digital camera and a digital video camera.

19. The method of claim 17, wherein said step of determining comprises correlating an identifying number of an individual animal and said liver.

20. The method of claim 17, wherein the drug is an antibiotic drug.

21. The method of claim 17, wherein the combination of drugs comprises at least one antibiotic drug.

22. A method for determining whether an animal was administered a drug, comprising:
    capturing an image of at least one lung of the animal by passing the at least one lung within the field of view of a means for generating an image;
    associating the image with a lot of origin of the animal;
    using a processor, analyzing the image to determine whether the at least one lung indicates that the animal has experienced infection or disease, said analyzing step comprising a review of visual evidence for the presence of lung abnormalities; and determining whether the animal was previously administered a drug or combination of drugs, said drug or combination of drugs comprising at least an antibiotic, and wherein said determining comprises correlating an identifying number of an individual animal with said at least one lung.

23. The method of claim 22, wherein the means for generating an image is selected from the group consisting of a digital color camera and a digital video camera.

* * * * *